(12) United States Patent
Loccufier

(10) Patent No.: US 8,759,412 B2
(45) Date of Patent: *Jun. 24, 2014

(54) POLYMERISABLE PHOTOINITIATORS FOR LED CURABLE COMPOSITIONS

(75) Inventor: Johan Loccufier, Zwijnaarde (BE)

(73) Assignee: Agfa Graphics NV, Mortsel (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/820,204

(22) PCT Filed: Oct. 4, 2011

(86) PCT No.: PCT/EP2011/067274
§ 371 (c)(1),
(2), (4) Date: Mar. 1, 2013

(87) PCT Pub. No.: WO2012/052288
PCT Pub. Date: Apr. 26, 2012

(65) Prior Publication Data
US 2013/0210954 A1     Aug. 15, 2013

Related U.S. Application Data

(60) Provisional application No. 61/406,593, filed on Oct. 26, 2010.

(30) Foreign Application Priority Data

Oct. 20, 2010   (EP) .................................... 10188140

(51) Int. Cl.
*B41M 5/28* (2006.01)
*C08F 2/50* (2006.01)
*C08F 2/46* (2006.01)
*A61L 2/08* (2006.01)
*A61L 24/00* (2006.01)
*C08G 61/04* (2006.01)

(52) U.S. Cl.
USPC ........... 522/53; 522/49; 522/6; 522/1; 522/71; 522/189; 522/184; 520/1

(58) Field of Classification Search
USPC ............. 522/53, 49, 6, 1, 71, 189, 184; 520/1
See application file for complete search history.

(56) References Cited

FOREIGN PATENT DOCUMENTS

| | | | |
|---|---|---|---|
| EP | 0 997 508 A1 | 5/2000 | |
| EP | 1 616 921 A1 | 1/2006 | |
| EP | 2 161 264 A1 | 3/2010 | |
| GB | 2009/060235 | * | 5/2009 |
| WO | 03/033492 A1 | 4/2003 | |
| WO | 2009/053305 A1 | 4/2009 | |
| WO | 2009/060235 A1 | 5/2009 | |
| WO | 2010/029017 A1 | 3/2010 | |
| WO | 2010/069758 A1 | 6/2010 | |

OTHER PUBLICATIONS

Official Communication issued in International Patent Application No. PCT/EP2011/067274, mailed on Dec. 8, 2011.
Loccufier, "LED Curable Compositions," U.S. Appl. No. 13/820,208, filed Mar. 1, 2013.
Allen et al., "Photochemistry and Photocuring Activity of Novel 1-Halogeno-4-propoxythioxanthones", Journal of the Chemical Society, Faraday Transactions, Royal Society of Chemistry, Cambridge, GB vol. 90, No. 1, 1994, pp. 83-92.

* cited by examiner

*Primary Examiner* — Ling Choi
*Assistant Examiner* — Jessica E Whiteley
(74) *Attorney, Agent, or Firm* — Keating & Bennett, LLP

(57) ABSTRACT

A polymerisable photoinitiator according to Formula (I):

Formula (I)

wherein:
R1 and R2 are independently selected from the group consisting of hydrogen, a substituted or unsubstituted alkyl group, a substituted or unsubstituted alkenyl group, a substituted or unsubstituted alkynyl group, a substituted or unsubstituted aralkyl group, a substituted or unsubstituted alkaryl group, a substituted or unsubstituted aryl or heteroaryl group, a halogen, an ether group, a thioether group, an aldehyde group, a ketone group, an ester group, an amide group, an amine and a nitro group;
$R^1$ and $R^2$ may represent the necessary atoms to form a five to eight membered ring;
L represents an n+m-valent linking group comprising 1 to 30 carbon atoms;
A represents a radically polymerizable group selected from the group consisting of an acrylate group, a methacrylate group, a styrene group, an acryl amide group, a methacryl amide group, a maleate group, a fumarate group, an itaconate group, a vinyl ether group, an allyl ether group, a vinyl ester group and an allyl ester group; and
n and m independently represent an integer from 1 to 5.

13 Claims, No Drawings

POLYMERISABLE PHOTOINITIATORS FOR LED CURABLE COMPOSITIONS

CROSS-REFERENCE TO RELATED APPLICATIONS

This application is a 371 National Stage Application of PCT/EP2011/067274, filed Oct. 4, 2011. This application claims the benefit of U.S. Provisional Application No. 61/406,593, filed Oct. 26, 2010, which is incorporated by reference herein in its entirety. In addition, this application claims the benefit of European Application No. 10188140.7, filed Oct. 20, 2010, which is also incorporated by reference herein in its entirety.

BACKGROUND OF THE INVENTION

1. Field of the Invention

The present invention relates to a new class of photoinitiators, especially suitable for low viscous radiation curable compositions that are curable by UV-LEDs and for packaging printing applications.

2. Description of the Related Art

Short run packaging printing is shifting from conventional printing techniques, such as offset printing, to digital printing, where ink jet is one of the preferred technologies. In inkjet printing, tiny drops of ink are projected directly onto an ink-receiver surface without physical contact between the printing device and the ink-receiver. The printing device stores the printing data electronically and controls a print head for ejecting the drops image-wise on an ink-receiver.

Within ink jet for digital packaging printing, there is a clear evolution towards higher image quality and higher printing speeds in combination with LED curing. In order to satisfy these demands, a new print head design is required. These print heads require a specific ink design as they only can operate with very low viscous inks. The inks for high resolution, high speed short run digital packaging printing have to combine low viscosity, low migrating properties after curing and high sensitivity for LED exposure.

Particularly interesting monomers to obtain low viscous ink jet inks have been described in EP 0997508 A (AGFA GEVAERT), which discloses radiation curable monomers containing vinylether and acrylate functions. Suitable monomers and radiation curable compositions having high degrees of conversion and low amounts of volatiles have also been disclosed in WO 2009/053305 (AGFA GRAPHICS).

High sensitivity for UV-LED exposure, preferably 395 nm LED exposure, requires bathochromic photoinitiators. Thioxanthones are known as being particularly preferred photoinitiators for LED exposure. For packaging applications, migration of photoinitiators has to be limited, leading to the need for diffusion hindered thioxanthones. A photoinitiator is considered diffusion hindered when it, for example, contains a polymeric group or at least one polymerizable group, e.g. an (meth)acrylate group.

Several diffusion hindered thioxanthones have been disclosed in the prior art. Polymeric thioxanthones have been disclosed in WO 03/033492 (COATES BROTHERS), WO 2009/060235 (LAMBSON LTD) and EP 1616921 A (AGFA GEVAERT). Polymerisable thioxanthones have been disclosed in EP 2161264 A (AGFA GRAPHICS) and WO 2010/069758 (AGFA GRAPHICS).

SUMMARY OF THE INVENTION

Within the class of thioxanthone photoinitiators, 1-chloro-4-alkoxy-thioxanthen-9-one based photoinitiators proved to be of particular interest in preparing radiation curable compositions exhibiting high curing speed with 395 nm-LEDs. However, it has been found that implementation of 1-chloro-4-alkoxy-thioxanthen-9-one type of photoinitiators in vinyl ether acrylate based compositions led to unacceptable formation of migratable and volatile degradation products.

Therefore, there is a need for diffusion hindered bathochromic photoinitiators, compatible with vinyl ether acrylate based ink compositions, enabling the design of LED-sensitive low viscous ink jet inks for packaging applications.

In order to overcome the problems described above, it has been surprisingly found that radiation curable compositions including a polymerisable photoinitiator as defined below could be cured at high curing speed upon exposure to UV radiation using 395 nm LEDs.

The polymerisable photoinitiator according to a preferred embodiment of the present invention has the advantage that it allows the formulation of ultra low viscous radiation curable compositions which cannot be obtained when employing polymeric photoinitiators as diffusion hindered photoinitiators.

The polymerisable photoinitiator according to a preferred embodiment of the present invention can be used in a wide range of radiation curable compositions which may be colourless or coloured, such as inkjet inks, flexographic inks and screen printing inks, because it has no or only a very limited contribution to the colour of the radiation curable composition.

The polymerisable photoinitiator according to a preferred embodiment of the present invention allows the formulation of radiation curable compositions having no or very limited smell after curing.

Other features, elements, steps, characteristics and advantages of the present invention will become more apparent from the following detailed description of preferred embodiments of the present invention hereinafter.

DETAILED DESCRIPTION OF THE PREFERRED EMBODIMENTS

The term "LED" is used in disclosing the present invention as an abbreviation for Light Emitting Diode.

The term "C.I." is used in disclosing the present invention as an abbreviation for Colour Index.

The term "alkyl" means all variants possible for each number of carbon atoms in the alkyl group i.e. for three carbon atoms: n-propyl and isopropyl; for four carbon atoms: n-butyl, isobutyl and tertiary-butyl; for five carbon atoms: n-pentyl, 1,1-dimethyl-propyl, 2,2-dimethylpropyl and 2-methyl-butyl etc.

The term "substituted", in e.g. substituted alkyl group means that the alkyl group may be substituted by other atoms than the atoms normally present in such a group, i.e. carbon and hydrogen. For example, a substituted alkyl group may include a halogen atom or a thiol group. An unsubstituted alkyl group contains only carbon and hydrogen atoms.

The term "monofunctional monomer" means a monomer having only one polymerizable group, for example an acrylate group.

The term "polyfunctional monomer" means a monomer having two, three or more polymerizable groups, e.g. two acrylate groups and one vinyl ether group.

Polymerizable Photoinitiators

The photoinitiator according to a preferred embodiment of the present invention is a polymerisable photoinitiator according to Formula (I):

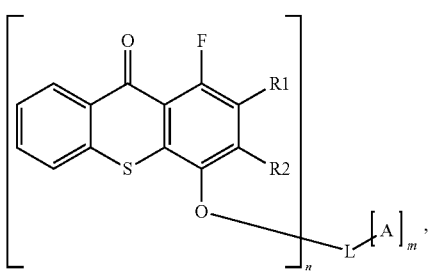

Formula (I)

wherein:
R¹ and R² are independently selected from the group consisting of hydrogen, a substituted or unsubstituted alkyl group, a substituted or unsubstituted alkenyl group, a substituted or unsubstituted alkynyl group, a substituted or unsubstituted aralkyl group, a substituted or unsubstituted alkaryl group, a substituted or unsubstituted aryl or heteroaryl group, a halogen, an ether group, a thioether group, an aldehyde group, a ketone group, an ester group, an amide group, an amine and a nitro group;
R¹ and R² may represent the necessary atoms to form a five to eight membered ring;
L represents an n+m-valent linking group comprising 1 to 30 carbon atoms;
A represents a radically polymerizable group selected from the group consisting of an acrylate group, a methacrylate group, a styrene group, an acryl amide group, a methacryl amide group, a maleate group, a fumarate group, an itaconate group, a vinyl ether group, an allyl ether group, a vinyl ester group and an allyl ester group; and
n and m independently represent an integer from 1 to 5.

In one preferred embodiment of the polymerisable photoinitiator, R¹ and R² both represent hydrogen.

In a preferred embodiment of the polymerisable photoinitiator, A represents an acrylate group and/or a methacrylate group, more preferably A represents an acrylate group.

The number of polymerizable groups m in the polymerisable photoinitiator according to Formula (I) is preferably an integer having a value of 1 to 5, more preferably an integer having a value of 2 to 4, most preferably m has the value of 2. With a value for m of 1 it is not excluded that unreacted polymerisable photoinitiator or degradation products thereof can still be found as an extractable from a cured composition containing the polymerisable photoinitiator. With values of m higher than 2, the photoinitiator is less mobile during the polymerization of the radiation curable composition and compounds having multiple polymerizable groups tend to reduce the flexibility of the cured composition. It was also observed that polymerisable photoinitiators containing more than one polymerizable group, preferably two polymerizable groups exhibited higher curing speeds.

In a preferred embodiment, the polymerisable photoinitiator according to the present invention is represented by Formula (II):

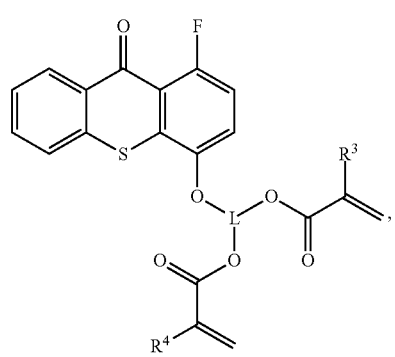

Formula (II)

wherein:
L represents a trivalent linking group comprising 1 to 30 carbon atoms; and
R³ and R⁴ independently represent hydrogen or a methyl group.

In a more preferred embodiment of the polymerisable photoinitiator according to Formula (II), both R³ and R⁴ represent hydrogen.

The type of linking group L in the polymerisable photoinitiator of Formula (I) and (II) comprising 1 to 30 carbon atoms is of minor importance to the functioning of the photoinitiator. It is preferably a substituted or unsubstituted alkylene group, a substituted or unsubstituted alkenyl group, a substituted or unsubstituted alkynyl group, a substituted or unsubstituted aralkyl group, a substituted or unsubstituted alkaryl group, a substituted or unsubstituted aryl or heteroaryl group.

Suitable examples of polymerisable photoinitiators, according to a preferred embodiment of the present invention are given by Table 1, without being limited thereto.

TABLE 1

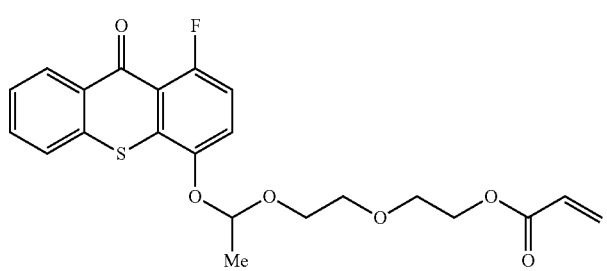

FTX-1

TABLE 1-continued
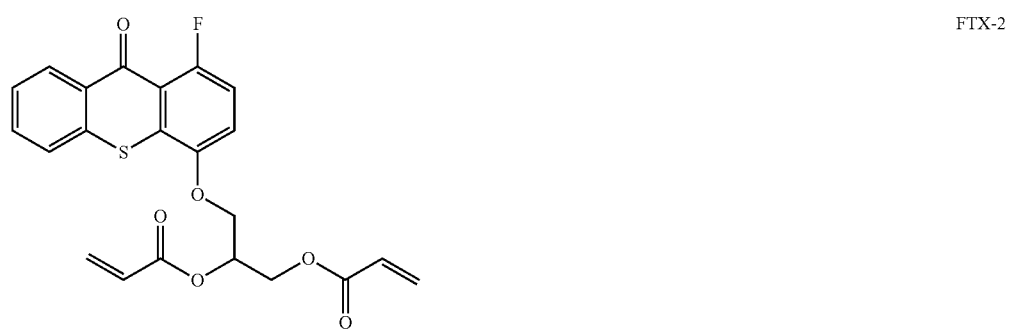 FTX-2
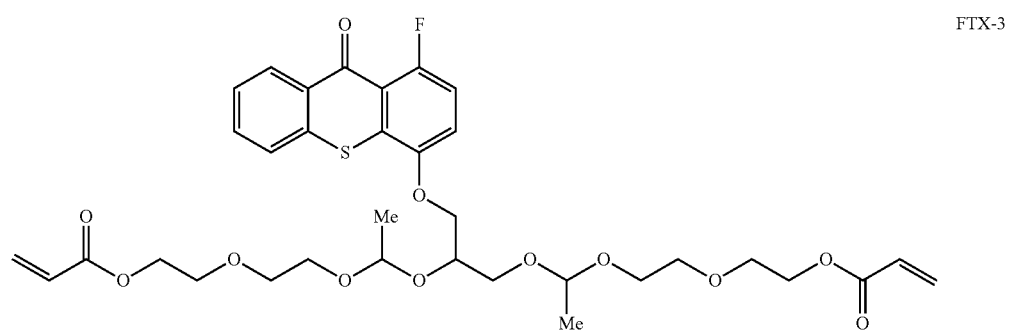 FTX-3
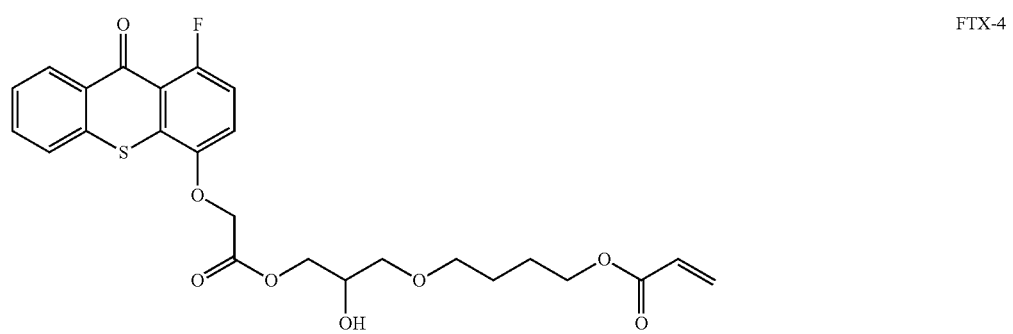 FTX-4
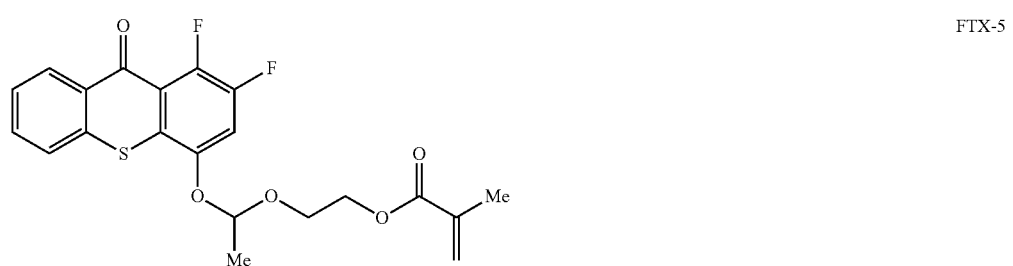 FTX-5
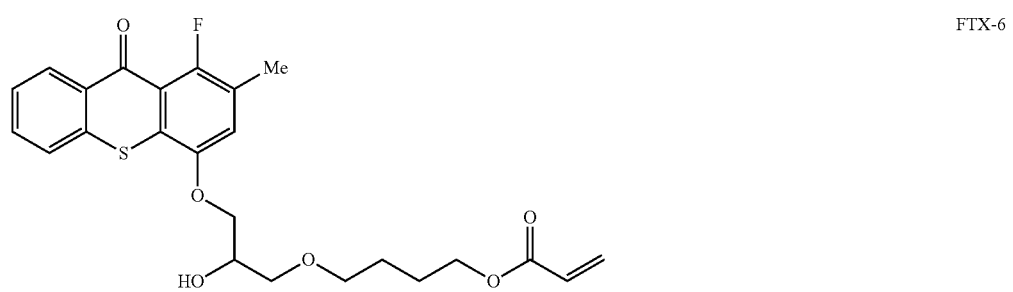 FTX-6

TABLE 1-continued

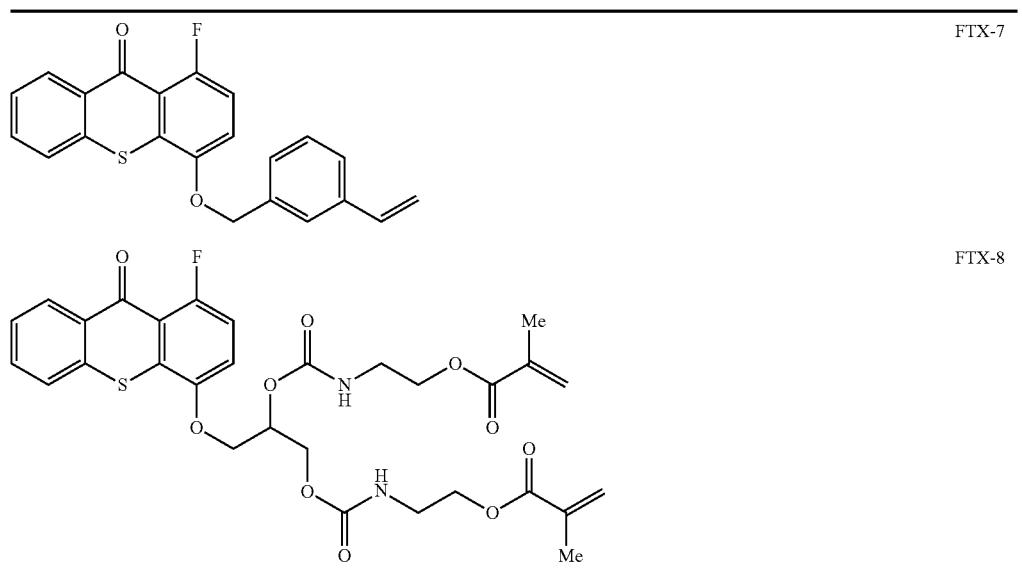

FTX-7

FTX-8

Method of Preparation of Polymerizable Photoinitiators

The method of preparing a polymerizable photoinitiator according to a preferred embodiment of the present invention includes the steps of:

a) providing a monomer according to Formula (III):

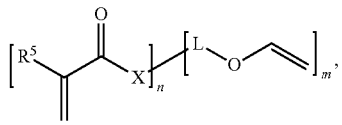

Formula (III)

wherein:
m and n independently represent an integer having a value from 1 to 5;
X represents O, S or $NR^6$;
$R^5$ and $R^6$ independently represent hydrogen or a substituted or unsubstituted alkyl group;
with the proviso that when $X=NR^6$ then L and $R^6$ may together form a ring system; and
L represents a linking group; and b) providing a photoinitiator according to Formula (Ia):

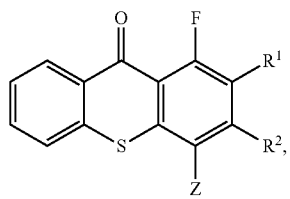

Formula (Ia)

wherein
$R^1$ and $R^2$ are independently selected from the group consisting of hydrogen, a substituted or unsubstituted alkyl group, a substituted or unsubstituted alkenyl group, a substituted or unsubstituted alkynyl group, a substituted or unsubstituted aralkyl group, a substituted or unsubstituted alkaryl group, a substituted or unsubstituted aryl or heteroaryl group, a halogen, an ether group, a thioether group, an aldehyde group, a ketone group, an ester group, an amide group, an amine and a nitro group; and
Z represents a hydroxyl group or an alkoxy group comprising at least one hydroxyl group; and c) catalyzing the reaction between the monomer and the photoinitiator with a catalyst to a polymerizable photoinitiator as defined above.

In a preferred embodiment of the photoinitiator according to Formula (Ia), $R^1$ and $R^2$ both represent hydrogen.

In a preferred embodiment of the photoinitiator according to Formula (Ia), Z represent a hydroxyl group.

In a more preferred embodiment when Z in Formula (Ia) represents a hydroxyl group, the hydroxyl group is first reacted with another compound, to allow incorporation of a plurality of radically polymerizable groups. For example, if this compound is 3-chloro-1,2-propanediol then two radically polymerizable groups can easily be introduced as exemplified by Example 1b here below for the incorporation of two acrylate groups.

In the most preferred embodiment, the reaction is performed in the absence of an organic solvent. The advantage is that organic solvents need not be removed, which is advantageous both for ecological reasons and when manufacturing radiation curable inkjet inks. These organic solvents tend to evaporate at the nozzles of an inkjet print head during a prolonged non-printing time. When restarting the printer, some nozzles appear to be clogged (=failing nozzles). Latency is the time that a print head can be left uncapped and idle before a failing nozzle appears.

Thus a great advantage of the present method for making the polymerizable photoinitiators is that no organic solvent is required but that the monomer according to Formula (III) can be used as the reaction medium. However, it remains possible in the method for preparing a polymerizable photoinitiator according to a preferred embodiment of the present invention to use one or more organic solvents in the synthesis.

The monomer according to Formula (III) is preferably used not only as reactant but also as reaction medium. The concentration of the monomer according to Formula (II) will be much larger than the concentration of the photoinitiator comprising at least one hydroxyl group. Preferably the molar ratio of the monomer according to Formula (II) over the photoinitiator comprising at least one hydroxyl group is at least 2, more preferably at least 5 and most preferably at least 7 or 10.

It is also possible to add other monomers to the reaction medium, even other monomers according to Formula (III). In the latter, a mixture of different polymerizable photoinitiators may be obtained depending on the concentration of the different monomers according to Formula (III).

After completion of the reaction the radiation curable composition includes at least a polymerizable photoinitiator according to Formula (I), a monomer according to Formula (III) and a catalyst. In a number of cases the catalyst may remain in the radiation curable composition if it does not interfere with the application or the curing of the curable composition. However, most preferably the catalyst is removed. The catalyst could be, for example, polymeric and could lead to an unacceptable viscosity for a UV curable inkjet ink.

The resulting composition including at least one monomer according to Formula (III) capable of free radical polymerization, and a polymerizable photoinitiator according to Formula (I) can directly be used for the formulation of radiation curable compositions and inks, for example, suitable for food packaging applications. This also has the advantage that solubility problems of an isolated photopolymerizable photoinitiator in a radiation curable composition can be avoided by optionally simply removing the catalyst and using the polymerizable photoinitiator dissolved in the monomer according to Formula (III) as such for addition to a radiation curable composition If required for a specific application, the polymerizable photoinitiator according to Formula (I), can be isolated and purified by any technique known in the prior art such as precipitation, crystallization and optionally chromatography.

Catalysts for preparing a polymerizable photoinitiator according to a preferred embodiment of the present invention include protic acids with a sufficient low $pK_a$, such as hydrochloric acid, phosphoric acid, sulfonic acids, sulfuric acid, and carboxylic acids substituted with electron withdrawing groups such as fluorine and chlorine.

Suitable catalysts include organic salts of sulfonic acids, such as pyridine salts. The use of sulfonic acids as catalyst has been disclosed in numerous documents (e.g. Munro et al., Bioorganic and Medicinal chemistry, 16(3), 1279-1286 (2008); Snowden et al. Helvetica Chimica Acta, 89(12), 3071-3086 (2006), Lucatelli et al., Journal of Organic Chemistry, 67(26), 9468-9470 (2002); Wipf et al., Tetrahedron Letters, 40(28), 5139-5142 (1999)) Typical examples are p.-toluene sulfonic acid, 10-camphor sulfonic acid and methane sulfonic acid.

The use of hydrochloric acid has been disclosed in several documents (e.g. Trofimov et al., Tetrahedron Letters, 49, 3104-3107 (2008)). The use of phosphoric acid has been disclosed by Toshiaki et al. (Tetrahedron Letters, 47, 3251-3255 (2006)).

The use of sulfuric acid has been described by Rappe et al. (Justus Liebigs Annalen der Chemie, 601, 84-111 (1956)).

The use of carboxylic acids, substituted with electron withdrawing substituents has been disclosed in a number of documents (e.g. Rivillo et al., Angewandte Chemie, International Edition, 46(38), 7247-72450 (2007); WO2007010483 (Firmenich S; A.); Alvarez de Cienfuego et al., Tetrahedron: asymmetry, 17(2), 1863-1866 (2006); US2005171062 (Allergan Inc.)). Typical examples are trifluoroacetic acid and trichloroacetic acid.

The use organic salts of sulfonic acids has been disclosed in several documents (Lee et al. Bulletin of the Korean Chemical Society, 28(4), 513-514 (2007); Hattori et al., Organic Letters, 10(5), 717-720 (2008); Nakamura et al., Organic Letters, 10(2), 309-312 (2008); Nicolau et al. Journal of the American chemical Society, 129(48), 14850-14851 (2007); Nakamura et al., Tetrahedron, 63(35), 8670-8676 (2007)). A typical example of an organic salt of a sulfonic acid is pyridinium tosylate. Occasionally, also Lewis acids have been reported as catalyst (Alper. H., Synthesis 1972, 81).

Several transition metals have also been shown effective as catalyst for the synthesis of asymmetric acetals from alkenylethers and alcohols (Maity, G; Synth Commun 1993, 23, 1667; Iqbal, J; Synth Commun 1989, 19, 901; Kantam, M; Synth Commun 1993, 23, 2225; Bhuma, V; Synth Commun 1992, 22, 2941; Ma, S; Tetrahedron Lett 1993, 34, 5269; Molnar, A; Tetrahedron Lett 1996, 37, 8597).

Heterogeneous catalysis has been reported frequently (Bongini, A; Synthesis 1979, 618; Johnston, R; Synthesis 1988, 393; Olah, G; Synthesis 1983, 892; Menger, F; J Org Chem 1981, 46, 5044; Hoyer, S; Synthesis 1986, 655; Upadhya, T; Synth Commun 1996, 26, 4539; Campelo, J; Synth Commun 1994, 24, 1345; Bandgar, B; Synth Commun 1995, 25, 2211; Kumar, P; Synthesis 1993, 1069; Chavez, F; Synth Commun 1992, 22, 159; Patney, H; Synth Commun 1991, 21, 2329; Campelo, J; Synth Commun 1992, 22, 2335).

Acetonyl triphenylphosphonium derivatives have also been reported as catalysts for converting alcohols into asymmetric acetals (Hon et al., Tetrahedron, 57, 5991-6001).

Particularly preferred catalysts are selected from the group consisting of a carboxylic acid substituted with an electron withdrawing group, an organic salt of a sulfonic acid and a heterogeneous catalyst, preferably selected from a salt of crosslinked vinylpyridine containing resins and crosslinked sulfonic acid containing resins.

The most preferred catalysts are selected from the group consisting of trifluoroacetic acid, trichloroacetic acid, pyridinium tosylate, crosslinked poly(vinylpyridine) hydrochloride, poly(vinylpyridinium) tosylate and sulfonic acid substituted ion exchangers.

The acetalysation catalyst can be removed by any technique known in the art. Preferably the catalyst is removed by filtration, neutralization, followed by filtration, neutralization on an ion exchanger or a basic resin and extraction.

Any suitable monomer according to Formula (III) may be used including those disclosed here below by Formula (IV), Formula (V) and in Table 2.

The synthesis of polymerisable photoinitiators of Formula (I) and (II) is exemplified in Examples 1a to 1d.

Radiation Curable Compositions

The polymerisable photoinitiator according to a preferred embodiment of the present invention can be used in any radiation curable composition, but is advantageously used for preparing low viscous radiation curable compositions such as inkjet inks and flexographic inks.

The polymerisable photoinitiator according to a preferred embodiment of the present invention can also be advantageously used in radiation curable compositions to reduce the amount of extractables and volatiles after curing, compared to e.g. other type of thioxanthone photoinitiators such as e.g. 1-chloro-4-alkoxy-thioxanthen-9-one based photoinitiators. This effect is especially observed for radiation curable compositions containing vinyletheracrylate monomers and derivatives thereof.

In one preferred embodiment, the radiation curable composition includes
a) a polymerisable photoinitiator according to a preferred embodiment of the present invention; and b) a monomer according to Formula (III):

$$\left[ R^5 \underset{\parallel}{\overset{O}{\text{C}}} X \right]_n \left[ L \overset{}{\text{O}} \diagup \right]_m$$

Formula (III)

wherein:
m and n independently represent an integer having a value from 1 to 5;
X represents O, S or NR$^6$;
R$^5$ and R$^6$ independently represent hydrogen or a substituted or unsubstituted alkyl group;
with the proviso that when X=NR$^6$ then L and R$^6$ may together form a ring system; and
L represents a linking group.

In a preferred embodiment, the monomer according to Formula (III) has a structure according to Formula (IV):

$$R^7 \underset{\parallel}{\overset{O}{\text{C}}} O - L - O \diagup$$

Formula (IV)

wherein:
R$^7$ represents a hydrogen or a methyl group; and
L represents a divalent linking group selected from the group consisting of a substituted or unsubstituted alkylene group, a substituted or unsubstituted alkenylene group, a substituted or unsubstituted alkynylene group, a substituted or unsubstituted cycloalkylene group and an ether containing alkylene group.

In the most preferred embodiment R$^7$ represents hydrogen.
In a further preferred embodiment, the monomer according to Formula (III) or (IV) has a structure according to Formula (V):

$$R^8 \underset{\parallel}{\overset{O}{\text{C}}} O \underset{}{\overset{}{\frown}} (O \underset{}{\frown})_n O \diagup$$

Formula (V)

wherein:
R$^8$ represents a hydrogen or a methyl group; and
n represents an integer from 0 to 4.

In the most preferred embodiment R$^8$ represents hydrogen and n is equal to 1.

Typical examples of monomers according to a preferred embodiment of the present invention are given by Table 2, without being limited thereto.

TABLE 2

| Structure | Name |
|---|---|
| (acrylate-OCH2CH2-O-CH2CH2-O-vinyl) | MONO-1 |
| (methacrylate-OCH2CH2-O-CH2CH2-O-vinyl) | MONO-2 |
| (methacrylate-OCH2CH2-O-vinyl) | MONO-3 |
| (acrylate-OCH2CH2-O-vinyl) | MONO-4 |
| (acrylate-O-(CH2)4-O-vinyl) | MONO-5 |
| (acrylate with neopentyl-Et quaternary carbon, O-vinyl) | MONO-6 |
| (diacrylate with quaternary carbon-Et, O-vinyl) | MONO-7 |
| (methacrylate-O-CH2-cyclohexyl-CH2-O-vinyl) | MONO-8 |
| (acrylate-O-CH2-CH=CH-CH2-O-vinyl) | MONO-9 |
| (glyceryl divinyl ether acrylate) | MONO-10 |
| (acrylate-O-(CH2)6-O-vinyl) | MONO-11 |

A single polymerizable photoinitiator according to a preferred embodiment of the present invention can be used in the radiation curable composition. However, the use of a mixture of one or more polymerizable photoinitiators according to a preferred embodiment of the present invention and optionally other photoinitiators, preferably diffusion hindered photoinitiators, is advantageous. The advantage is that the absorption spectrum of UV radiation is enlarged and/or synergistic effects between photoinitiators are obtained, thereby speeding up the polymerization of the monomers and oligomers in the radiation curable composition.

Both type I and type II photoinitiators can be used in a preferred embodiment of the present invention, alone or in combination. A Norrish Type I initiator is an initiator which cleaves after excitation, yielding the initiating radical immediately. A Norrish type II-initiator is a photoinitiator which is activated by actinic radiation and forms free radicals by hydrogen abstraction from a second compound that becomes the actual initiating free radical. This second compound is called a polymerization synergist or co-initiator.

Suitable photo-initiators are disclosed in CRIVELLO, J. V., et al. VOLUME III: Photoinitiators for Free Radical Cationic. 2nd edition. Edited by BRADLEY, G. London, UK: John Wiley and Sons Ltd, 1998. p. 287-294. Preferably diffusion hindered analogues of these photoinitiators are used.

A diffusion hindered photoinitiator is a photoinitiator which exhibits a much lower mobility in a cured layer of the curable composition or ink than a monofunctional photoinitiator, such as benzophenone. Several methods can be used to lower the mobility of the photoinitiator. One way is to increase the molecular weight of the photoinitiator so that the diffusion speed is reduced, e.g. polymeric photoinitiators. Another way is to increase its reactivity so that it is built into the polymerizing network, e.g. multifunctional photoinitiators (having 2, 3 or more photoinitiating groups) and polymerizable photoinitiators. The diffusion hindered photoinitiator is preferably selected from the group consisting of non-polymeric multifunctional photoinitiators, polymeric photoinitiators and polymerizable photoinitiators. Non-polymeric di- or multifunctional photoinitiators usually have a molecular weight between 300 and 900 Dalton. Non-polymerizable monofunctional photoinitiators with a molecular weight in that range are not diffusion hindered photoinitiators. Most preferably the diffusion hindered photoinitiator is a polymerizable initiator since the effect on viscosity increase of the radiation curable composition is much smaller compared to other type of diffusion hindered initiators such as polymeric photoinitiators.

A suitable diffusion hindered photoinitiator may contain one or more photoinitiating functional groups derived from a Norrish type I-photoinitiator selected from the group consisting of benzoinethers, benzil ketals, $\alpha,\alpha$-dialkoxyacetophenones, $\alpha$-hydroxyalkylphenones, $\alpha$-aminoalkylphenones, acylphosphine oxides, acylphosphine sulfides, $\alpha$-haloketones, $\alpha$-halosulfones and phenylglyoxalates.

A suitable diffusion hindered photoinitiator may contain one or more photoinitiating functional groups derived from a Norrish type II-initiator selected from the group consisting of benzophenones, thioxanthones, 1,2-diketones and anthraquinones.

Suitable diffusion hindered photoinitiators are also those disclosed in EP 2053101 A (AGFA GRAPHICS) in paragraphs [0074] and [0075] for difunctional and multifunctional photoinitiators, in paragraphs [0077] to [0080] for polymeric photoinitiators and in paragraphs [0081] to [0083] for polymerizable photoinitiators.

Other preferred polymerizable photoinitiators are those disclosed in EP 2065362 A (AGFA GRAPHICS) and EP 2161264 A (AGFA GRAPHICS), incorporated herein by reference.

A preferred amount of photoinitiator is 0-50 wt %, more preferably 0.1-20 wt %, and most preferably 0.3-15 wt % of the total weight of the curable pigment dispersion or ink.

The radiation curable composition preferably includes at least one colorant, but can also be a colourless liquid. In the case of radiation curable inkjet inks, such a colourless inkjet ink can, for example, be used to enhance the glossiness of an inkjet printed image.

The radiation curable compositions are preferably non-aqueous compositions. The term "non-aqueous" refers to a liquid carrier which should contain no water. However sometimes a small amount, generally less than 5 wt % of water based on the total weight of the composition or ink, can be present. This water was not intentionally added but came into the composition via other components as a contamination, such as for example polar organic solvents. Higher amounts of water than 5 wt % tend to make the radiation curable compositions and inks instable, preferably the water content is less than 1 wt % based on the total weight of radiation curable composition or ink and most preferably no water at all is present The radiation curable compositions and inks preferably do not contain an evaporable component such as an organic solvent. But sometimes it can be advantageous to incorporate a small amount of an organic solvent to improve adhesion to the surface of a substrate after UV-curing. In this case, the added solvent can be any amount in the range that does not cause problems of solvent resistance and VOC, and preferably 0.1-10.0 wt %, and particularly preferably 0.1-5.0 wt %, each based on the total weight of the curable composition.

The radiation curable composition is preferably a radiation curable inkjet ink including no organic solvent or water.

A free radical radiation curable inkjet ink set includes at least two different inkjet inks, wherein at least one inkjet ink preferably contains one or more colorants, preferably one or more colour pigments.

The curable ink set preferably comprises at least one yellow curable ink (Y), at least one cyan curable ink (C) and at least one magenta curable ink (M) and preferably also at least one black curable ink (K). The curable CMYK-ink set may also be extended with extra inks such as red, green, blue, and/or orange to further enlarge the colour gamut of the image. The CMYK-ink set may also be extended by the combination of the full density inkjet inks with light density inkjet inks. The combination of dark and light colour inks and/or black and grey inks improves the image quality by a lowered graininess.

The pigmented radiation curable ink preferably contains a dispersant, more preferably a polymeric dispersant, for dispersing the pigment. The pigmented curable ink may contain a dispersion synergist to improve the dispersion quality and stability of the ink. Preferably, at least the magenta ink contains a dispersion synergist. A mixture of dispersion synergists may be used to further improve dispersion stability.

The viscosity of the radiation curable composition or inkjet ink is preferably smaller than 20 mPa·s at 45° C. and at a shear rate of 1,000 s$^{-1}$, more preferably between 1 and 14 mPa·s at 45° C. and a shear rate of 1,000 s$^{-1}$.

For high speed, high resolution printing, the viscosity measured at 45° C. is preferably smaller than 10 mPa·s at 45° C. and at a shear rate of 90 s$^{-1}$. Such measurement can be performed using a Brookfield DV-II+ viscometer at 45° C. and at 12 rotations per minute.

The surface tension of the curable composition or inkjet ink is preferably in the range of about 20 mN/m to about 70 mN/m at 25° C., more preferably in the range of about 22 mN/m to about 40 mN/m at 25° C.

The curable composition or inkjet ink may further also contain at least one inhibitor for improving the thermal stability of the ink.

The curable composition or inkjet ink may further also contain at least one surfactant for obtaining good spreading characteristics on a substrate.

Monomers and Oligomers

The monomers and oligomers used in radiation curable compositions and inks, especially for food packaging applications, are preferably purified compounds having no or almost no impurities, more particularly no toxic or carcinogenic impurities. The impurities are usually derivative compounds obtained during synthesis of the polymerizable compound. Sometimes, however, some compounds may be added deliberately to pure polymerizable compounds in harmless amounts, for example, polymerization inhibitors or stabilizers.

Any monomer or oligomer capable of free radical polymerization may be used as polymerizable compound. A combination of monomers, oligomers and/or prepolymers may also be used. The monomers, oligomers and/or prepolymers may possess different degrees of functionality, and a mixture including combinations of mono-, di-, tri- and higher functionality monomers, oligomers and/or prepolymers may be used. The viscosity of the radiation curable compositions and inks can be adjusted by varying the ratio between the monomers and oligomers.

Particularly preferred monomers and oligomers are those listed in [0106] to [0115] in EP 1911814 A (AGFA GRAPHICS) incorporated herein as a specific reference.

Co-Initiators

In order to increase the photosensitivity further, the radiation curable composition or ink may additionally contain co-initiators. Suitable examples of co-initiators can be categorized in three groups:

(1) tertiary aliphatic amines such as methyldiethanolamine, dimethylethanolamine, triethanolamine, triethylamine and N-methylmorpho line;
(2) aromatic amines such as amylparadimethylaminobenzoate, 2-n-butoxyethyl-4-(dimethylamino) benzoate, 2-(dimethylamino)ethylbenzoate, ethyl-4-(dimethylamino)benzoate, and 2-ethylhexyl-4-(dimethylamino) benzoate; and
(3) (meth)acrylated amines such as dialkylamino alkyl(meth) acrylates (e.g., diethylaminoethylacrylate) or N-morpholinoalkyl-(meth)acrylates (e.g., N-morpholinoethyl-acrylate).

The preferred co-initiators are aminobenzoates.

When one or more co-initiators are included into the radiation curable composition, preferably these co-initiators are diffusion hindered for safety reasons, in particular for food packaging applications.

A diffusion hindered co-initiator is preferably selected from the group consisting of non-polymeric di- or multifunctional co-initiators, oligomeric or polymeric co-initiators and polymerizable co-initiators. More preferably the diffusion hindered co-initiator is selected from the group consisting of polymeric co-initiators and polymerizable co-initiators. Most preferably the diffusion hindered co-initiator is a polymerizable co-initiator having at least one (meth)acrylate group, more preferably having at least one acrylate group.

In a further preferred embodiment, the photoinitiators according to the present invention are used in a radiation curable composition comprising at least one oligomeric, multifunctional or polymerisable ethylenically unsaturated co-initiator, selected from the group consisting of aliphatic tertiary amines and dialkylamino substituted aromatic compounds, dialkylamino substituted aromatic compounds being preferred, 4-dialkylamino benzoic acid derivatives being the most preferred.

Suitable examples of oligomeric co-initiators are given by Table 3 without being limited thereto.

TABLE 3

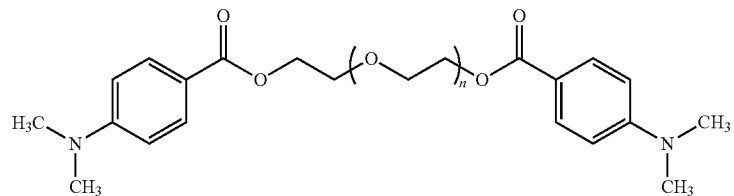

OCI-1 n: 13 on average

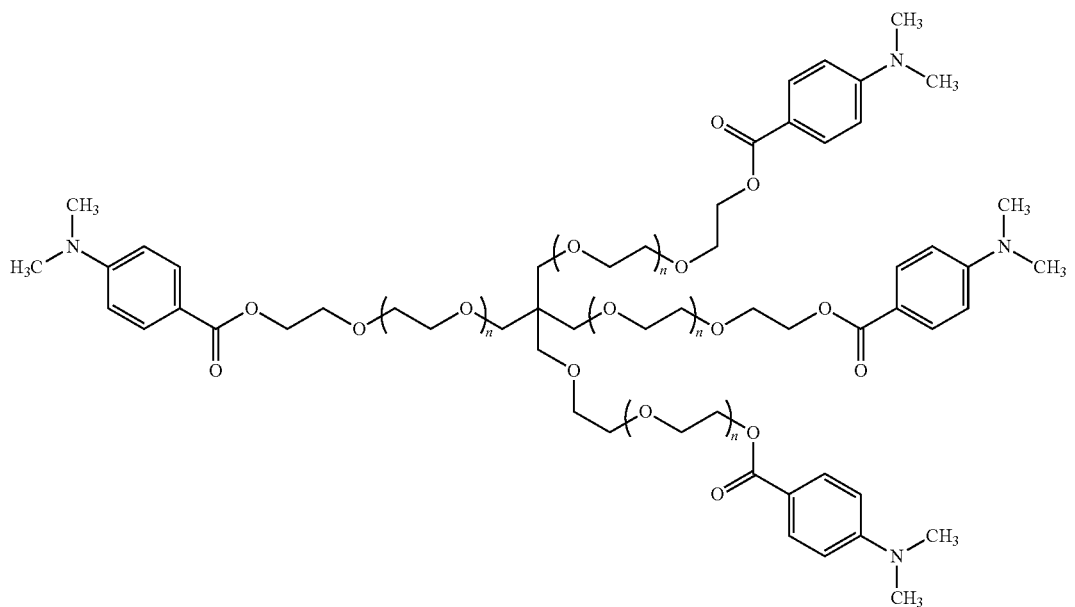

OCI-2 n: 3 on average

TABLE 3-continued

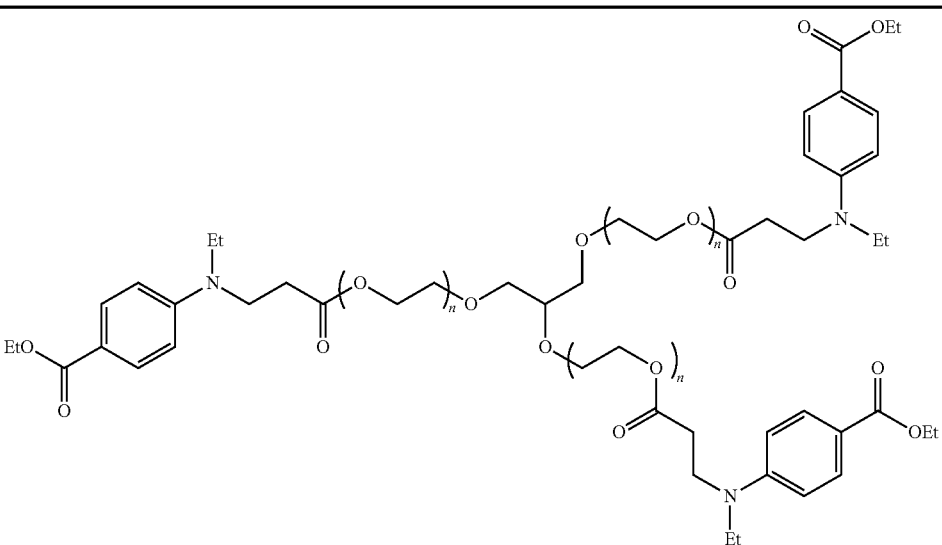

n: 7 on average

Oligomeric co-initiators differ from multifunctional co-initiators in that oligomeric co-initiators have a weight distribution and an average molecular weight $M_w$, while multifunctional co-initiators have only one distinct molecular weight and chemical structure. For example, the olgimeric co-initiator OCI-1 in Table 3 may include the multifunctional co-initiator MCI-7 of Table 4. Oligomeric co-initiators also have a molecular weight smaller than about 1500. Preferred polymeric co-initiators are hyperbranched polymeric co-initiators as disclosed by EP 1616897 A (AGFA).

Suitable examples of multifunctional co-initiators are given by Table 4, without being limited thereto.

TABLE 4

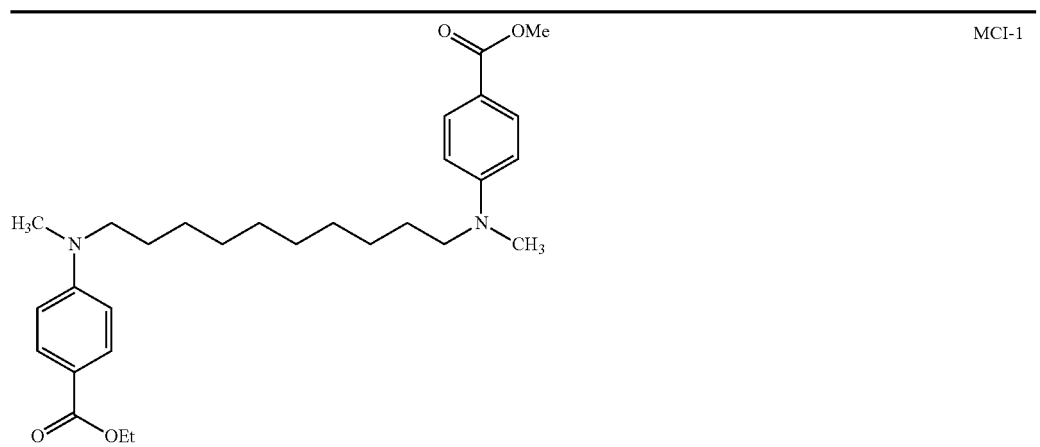

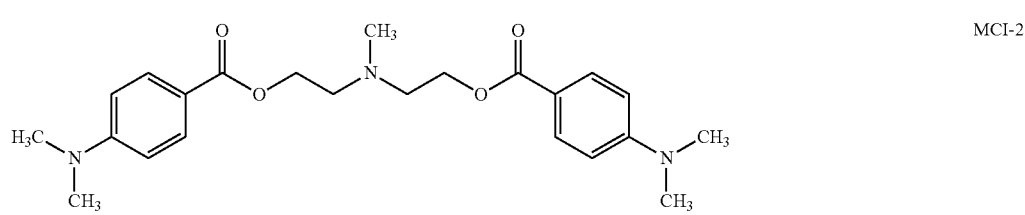

TABLE 4-continued
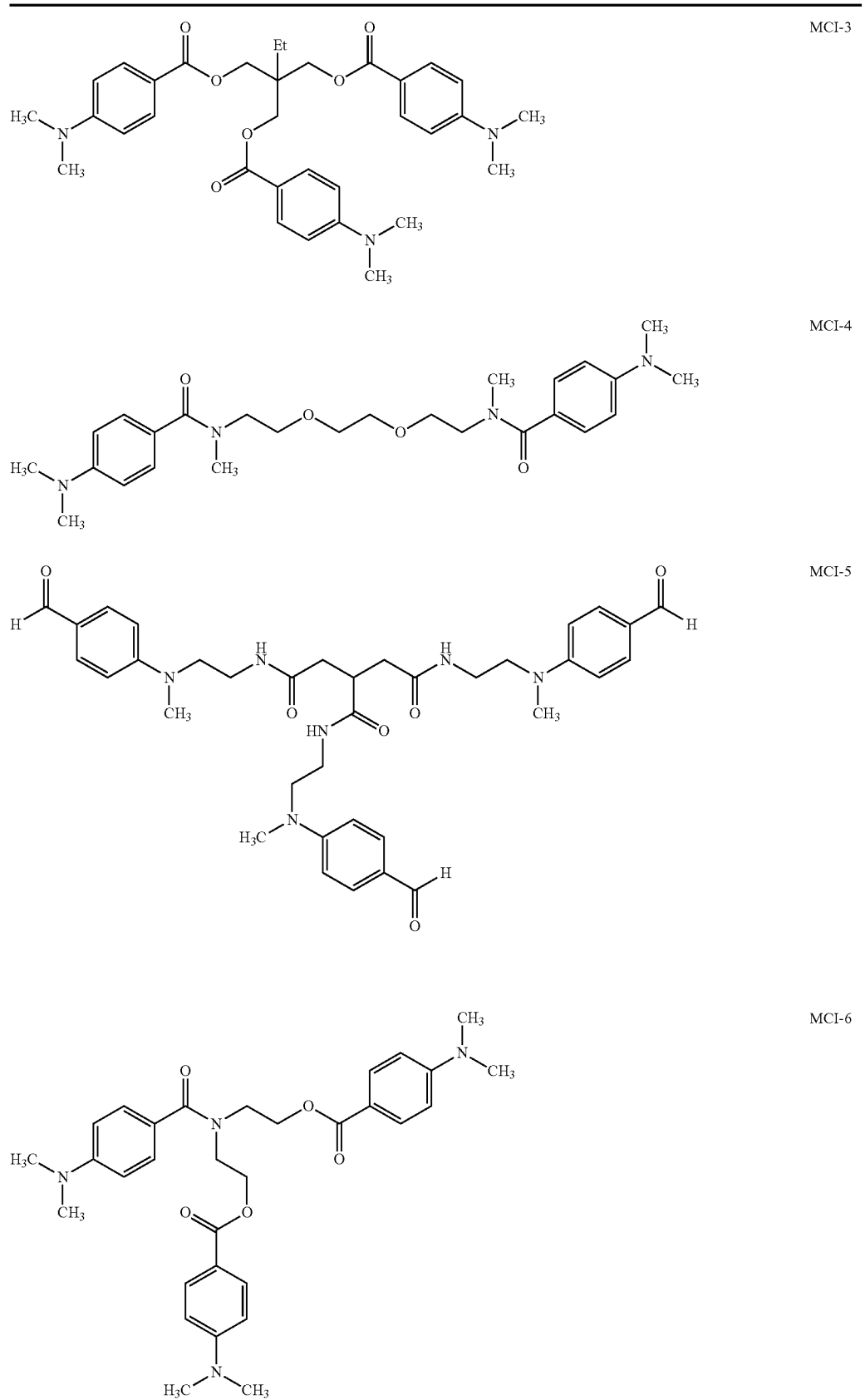
MCI-3
MCI-4
MCI-5
MCI-6

TABLE 4-continued
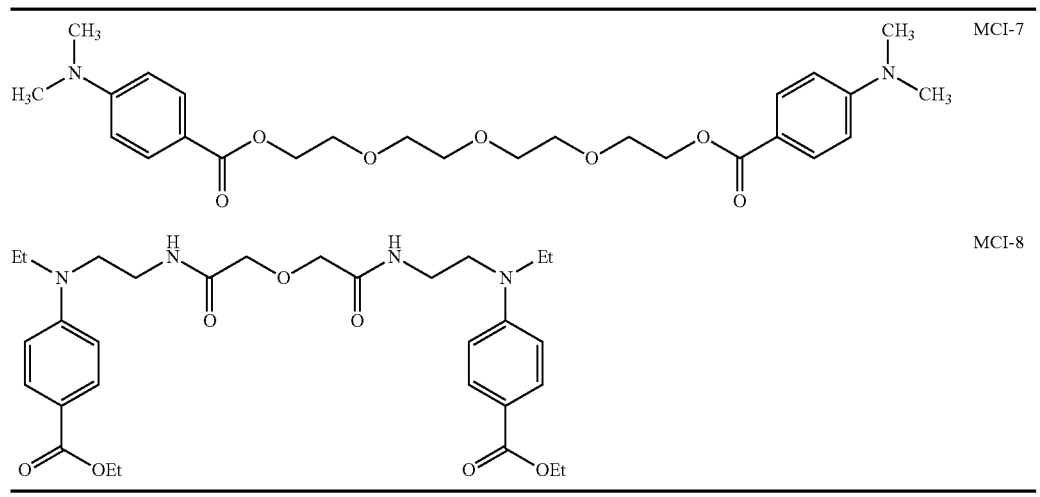
Suitable examples of polymerisable ethylenically unsaturated co-initiators are given by Table 5, without being limited thereof.
TABLE 5
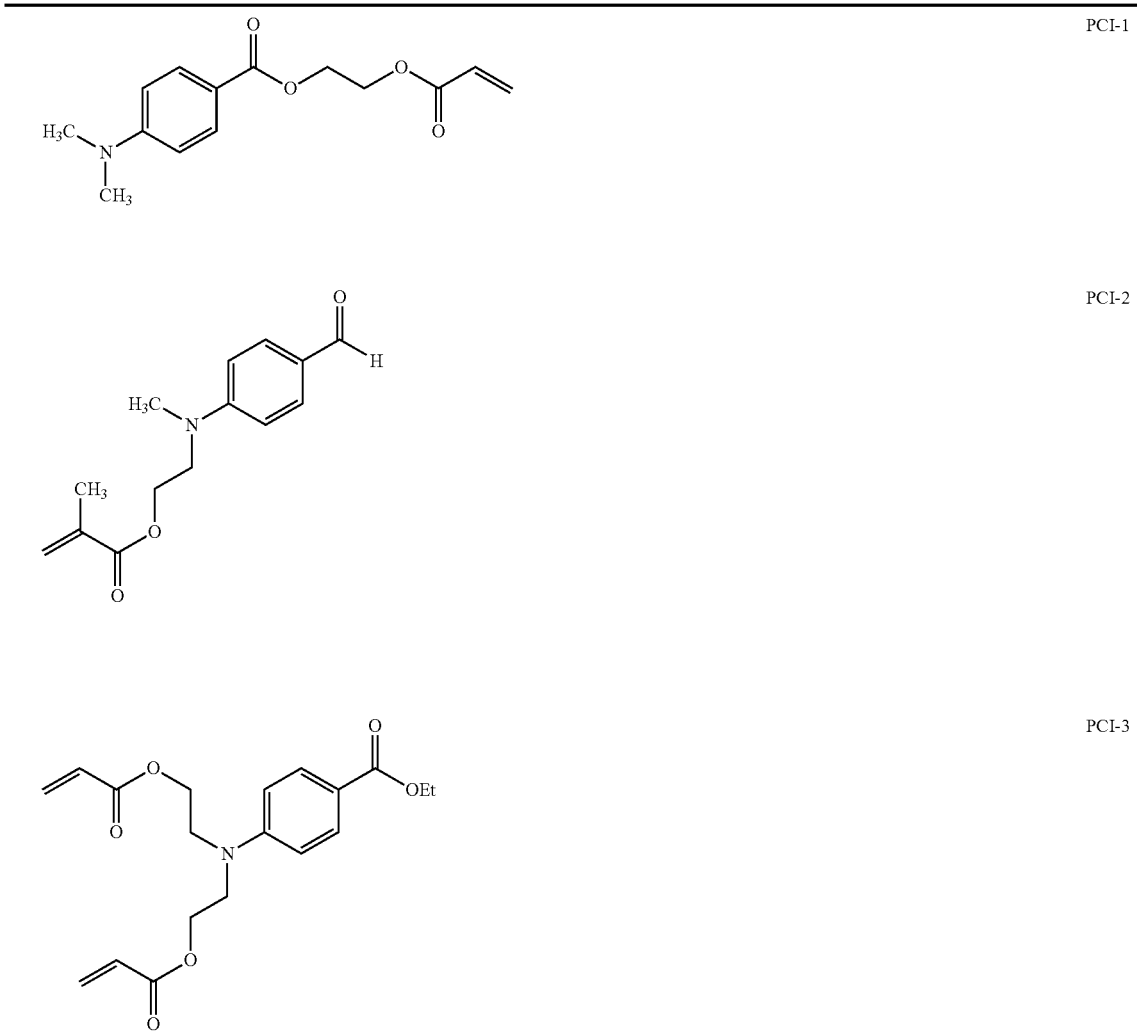

TABLE 5-continued
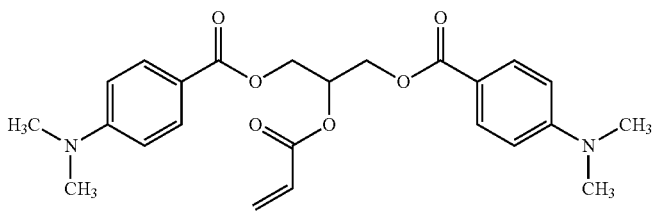 PCI-4
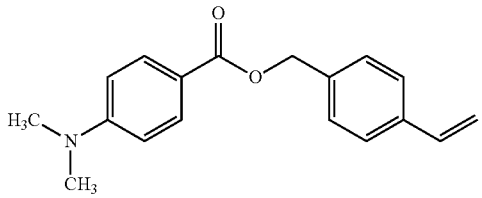 [SMILES: C=Cc1ccc(COC(=O)c2ccc(N(C)C)cc2)cc1] PCI-5
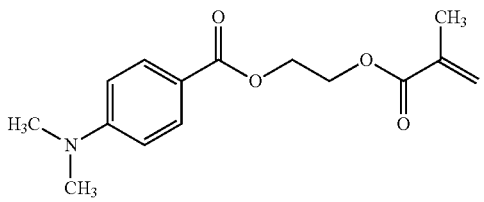 [SMILES: C=C(C)C(=O)OCCOC(=O)c1ccc(N(C)C)cc1] PCI-6
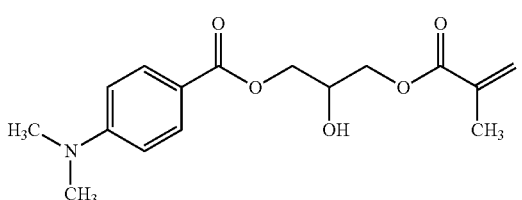 PCI-7
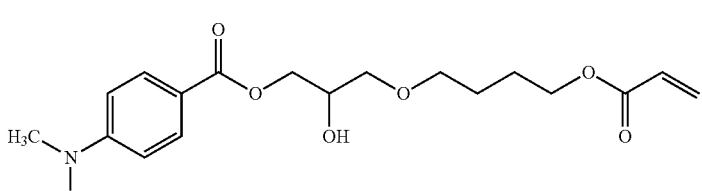 PCI-8
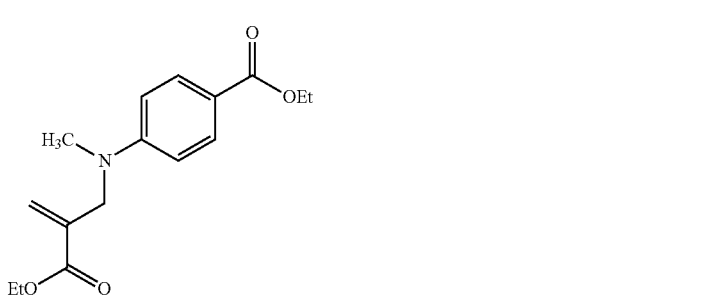 [SMILES: C=C(CN(C)c1ccc(C(=O)OCC)cc1)C(=O)OCC] PCI-9
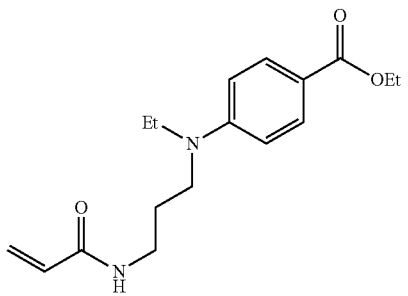 [SMILES: C=CC(=O)NCCCN(CC)c1ccc(C(=O)OCC)cc1] PCI-10

TABLE 5-continued

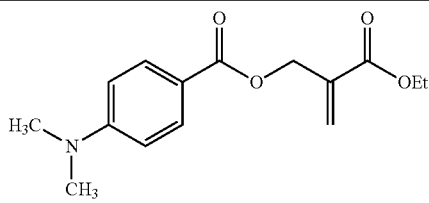
PCI-11

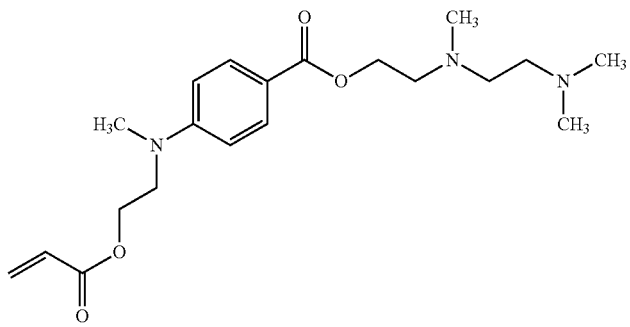 [SMILES: C=CC(=O)OCCN(C)c1ccc(C(=O)OCCN(C)CCN(C)C)cc1]
PCI-12

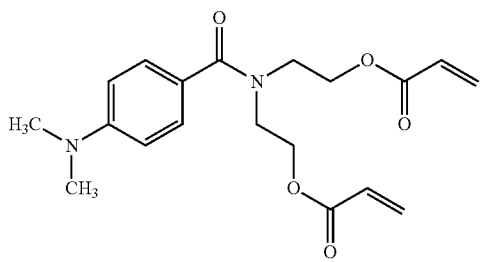 [SMILES: C=CC(=O)OCCN(CCOC(=O)C=C)C(=O)c1ccc(N(C)C)cc1]
PCI-13

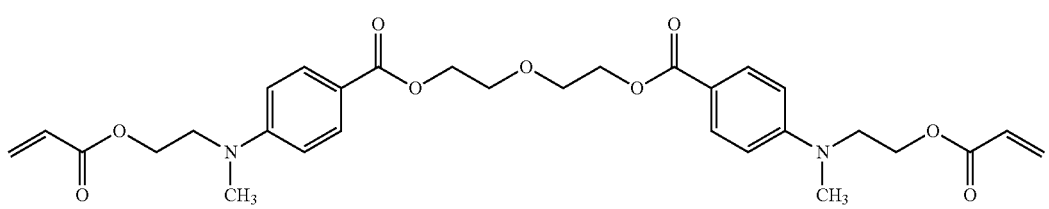 [SMILES: C=CC(=O)OCCN(C)c1ccc(C(=O)OCCOCCOC(=O)c2ccc(N(C)CCOC(=O)C=C)cc2)cc1]
PCI-14

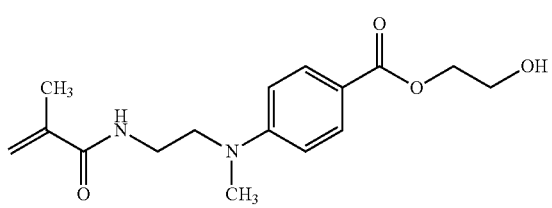 [SMILES: C=C(C)C(=O)NCCN(C)c1ccc(C(=O)OCCO)cc1]
PCI-15

The radiation curable composition preferably comprises the diffusion hindered co-initiator in an amount of 0.1 to 50 wt %, more preferably in an amount of 0.5 to 25 wt %, most preferably in an amount of 1 to 10 wt % of the total weight of the radiation curable composition.

Inhibitors

The radiation curable compositions and inks may contain a polymerization inhibitor. Suitable polymerization inhibitors include phenol type antioxidants, hindered amine light stabilizers, phosphor type antioxidants, hydroquinone monomethyl ether commonly used in (meth)acrylate monomers, and hydroquinone, t-butylcatechol, pyrogallol, 2,6-di-tert.butyl-4-methylphenol (=BHT) may also be used.

Suitable commercial inhibitors are, for example, SUMILIZER™ GA-80, SUMILIZER™ GM and SUMILIZER™ GS produced by Sumitomo Chemical Co. Ltd.; GENORAD™ 16, GENORAD™ 18 and GENORAD™ 20 from Rahn A G; IRGASTAB™ UV10 and IRGASTAB™ UV22, TINUVIN™ 460 and CGS20 from Ciba Specialty Chemicals; FLOORSTAB™ UV range (UV-1, UV-2, UV-5 and UV-8) from Kromachem Ltd, ADDITOL™ S range (S100, 5110, 5120 and 5130) from Cytec Surface Specialties.

The inhibitor is preferably a polymerizable inhibitor.

Since excessive addition of these polymerization inhibitors may lower the curing speed, it is preferred that the amount capable of preventing polymerization is determined prior to blending. The amount of a polymerization inhibitor is preferably lower than 5 wt %, more preferably lower than 3 wt % of the total radiation curable composition or ink.

Colorants

Colorants used in the radiation curable compositions may be dyes, pigments or a combination thereof. Organic and/or inorganic pigments may be used. The colorant is preferably a pigment or a polymeric dye, most preferably a pigment.

The pigments may be black, white, cyan, magenta, yellow, red, orange, violet, blue, green, brown, mixtures thereof, and the like. A colour pigment may be chosen from those disclosed by HERBST, Willy, et al. Industrial Organic Pigments, Production, Properties, Applications. 3rd edition. Wiley—VCH, 2004. ISBN 3527305769.

Suitable pigments are disclosed in paragraphs [0128] to [0138] of WO 2008/074548 (AGFA GRAPHICS).

Also mixed crystals may be used. Mixed crystals are also referred to as solid solutions. For example, under certain conditions different quinacridones mix with each other to form solid solutions, which are quite different from both physical mixtures of the compounds and from the compounds themselves. In a solid solution, the molecules of the components enter into the same crystal lattice, usually, but not always, that of one of the components. The x-ray diffraction pattern of the resulting crystalline solid is characteristic of that solid and can be clearly differentiated from the pattern of a physical mixture of the same components in the same proportion. In such physical mixtures, the x-ray pattern of each of the components can be distinguished, and the disappearance of many of these lines is one of the criteria of the formation of solid solutions. A commercially available example is CINQUASIA™ Magenta RT-355-D from Ciba Specialty Chemicals.

Also mixtures of pigments may be used in the pigment dispersions. For some inkjet applications, a neutral black inkjet ink is preferred and can be obtained, for example, by mixing a black pigment and a cyan pigment into the ink. The inkjet application may also require one or more spot colours, for example for packaging inkjet printing or textile inkjet printing. Silver and gold are often desired colours for inkjet poster printing and point-of-sales displays.

Non-organic pigments may be used in the pigment dispersions. Particular preferred pigments are C.I. Pigment Metal 1, 2 and 3. Illustrative examples of the inorganic pigments include red iron oxide (III), cadmium red, ultramarine blue, prussian blue, chromium oxide green, cobalt green, amber, titanium black and synthetic iron black.

Pigment particles in inkjet inks should be sufficiently small to permit free flow of the ink through the inkjet-printing device, especially at the ejecting nozzles. It is also desirable to use small particles for maximum colour strength and to slow down sedimentation.

The numeric average pigment particle size is preferably between 0.050 and 1 μm, more preferably between 0.070 and 0.300 μm and particularly preferably between 0.080 and 0.200 μm. Most preferably, the numeric average pigment particle size is no larger than 0.150 μm. An average particle size smaller than 0.050 μm is less desirable for decreased light-fastness, but mainly also because very small pigment particles or individual pigment molecules thereof may still be extracted in food packaging applications. The average particle size of pigment particles is determined with a Brookhaven Instruments Particle Sizer BI90plus based upon the principle of dynamic light scattering. The ink is diluted with ethyl acetate to a pigment concentration of 0.002 wt %. The measurement settings of the BI90plus are: 5 runs at 23° C., angle of 90°, wavelength of 635 nm and graphics=correction function However for white pigment dispersions, the numeric average particle diameter of the white pigment is preferably from 50 to 500 nm, more preferably from 150 to 400 nm, and most preferably from 200 to 350 nm. Sufficient hiding power cannot be obtained when the average diameter is less than 50 nm, and the storage ability and the jet-out suitability of the ink tend to be degraded when the average diameter exceeds 500 nm. The determination of the numeric average particle diameter is best performed by photon correlation spectroscopy at a wavelength of 633 nm with a 4 mW HeNe laser on a diluted sample of the pigmented inkjet ink. A suitable particle size analyzer used was a MALVERN™ nano-S available from Goffin-Meyvis. A sample can, for example, be prepared by addition of one drop of ink to a cuvette containing 1.5 mL ethyl acetate and mixed until a homogenous sample was obtained. The measured particle size is the average value of 3 consecutive measurements consisting of 6 runs of 20 seconds.

Suitable white pigments are given by Table 2 in [0116] of WO 2008/074548 (AGFA GRAPHICS). The white pigment is preferably a pigment with a refractive index greater than 1.60. The white pigments may be employed singly or in combination. Preferably titanium dioxide is used as pigment with a refractive index greater than 1.60. Suitable titanium dioxide pigments are those disclosed in [0117] and in [0118] of WO 2008/074548 (AGFA GRAPHICS).

The pigments are preferably present in the range of 0.01 to 15%, more preferably in the range of 0.05 to 10% by weight and most preferably in the range of 0.1 to 5% by weight, each based on the total weight of the pigment dispersion. For white pigment dispersions, the white pigment is preferably present in an amount of 3% to 30% by weight of the pigment dispersion, and more preferably 5% to 25%. An amount of less than 3% by weight cannot achieve sufficient covering power and usually exhibits very poor storage stability and ejection property.

Dispersants

The dispersant is preferably a polymeric dispersant. Typical polymeric dispersants are copolymers of two monomers but may contain three, four, five or even more monomers. The properties of polymeric dispersants depend on both the nature of the monomers and their distribution in the polymer. Suitable copolymeric dispersants have the following polymer compositions:

statistically polymerized monomers (e.g. monomers A and B polymerized into ABBAABAB);

alternating polymerized monomers (e.g. monomers A and B polymerized into ABABABAB);

gradient (tapered) polymerized monomers (e.g. monomers A and B polymerized into AAABAABBABBB);

block copolymers (e.g. monomers A and B polymerized into AAAAABBBBBB) wherein the block length of each of the blocks (2, 3, 4, 5 or even more) is important for the dispersion capability of the polymeric dispersant;

graft copolymers (graft copolymers consist of a polymeric backbone with polymeric side chains attached to the backbone); and mixed forms of these polymers, e.g. blocky gradient copolymers.

Suitable polymeric dispersants are listed in the section on "Dispersants", more specifically [0064] to [0070] and to [0077], in EP 1911814 A (AGFA GRAPHICS) incorporated herein as a specific reference.

The polymeric dispersant has preferably a number average molecular weight Mn between 500 and 30000, more preferably between 1500 and 10000.

The polymeric dispersant has preferably a weight average molecular weight Mw smaller than 100000, more preferably smaller than 50000 and most preferably smaller than 30000.

The polymeric dispersant has preferably a polydispersity PD smaller than 2, more preferably smaller than 1.75 and most preferably smaller than 1.5.

Commercial examples of polymeric dispersants are the following:
- DISPERBYK™ dispersants available from BYK CHEMIE GMBH;
- SOLSPERSE™ dispersants available from NOVEON;
- TEGO™ DISPERS™ dispersants from EVONIK;
- EDAPLAN™ dispersants from MÜNZING CHEMIE;
- ETHACRYL™ dispersants from LYONDELL;
- GANEX™ dispersants from ISP;
- DISPEX™ and EFKA™ dispersants from CIBA SPECIALTY CHEMICALS INC (BASF);
- DISPONER™ dispersants from DEUCHEM; and
- JONCRYL™ dispersants from JOHNSON POLYMER.

Particularly preferred polymeric dispersants include SOLSPERSE™ dispersants from NOVEON, EFKA™ dispersants from CIBA SPECIALTY CHEMICALS INC (BASF) and DISPERBYK™ dispersants from BYK CHEMIE GMBH. Particularly preferred dispersants are SOLSPERSE™ 32000, 35000 and 39000 dispersants from NOVEON.

The polymeric dispersant is preferably used in an amount of 2 to 600 wt %, more preferably 5 to 200 wt % based on the weight of the pigment.

Dispersion Synergists

A dispersion synergist usually consists of an anionic part and a cationic part. The anionic part of the dispersion synergist exhibiting a certain molecular similarity with the colour pigment and the cationic part of the dispersion synergist consists of one or more protons and/or cations to compensate the charge of the anionic part of the dispersion synergist.

The synergist is preferably added in a smaller amount than the polymeric dispersant(s). The ratio of polymeric dispersant/dispersion synergist depends upon the pigment and should be determined experimentally. Typically the ratio wt % polymeric dispersant/wt % dispersion synergist is selected between 2:1 to 100:1, preferably between 2:1 and 20:1.

Suitable dispersion synergists that are commercially available include SOLSPERSE™ 5000 and SOLSPERSE™ 22000 from NOVEON.

Particular preferred pigments for the magenta ink used are a diketopyrrolo-pyrrole pigment or a quinacridone pigment. Suitable dispersion synergists include those disclosed in EP 1790698 A (AGFA GRAPHICS), EP 1790696 A (AGFA GRAPHICS), WO 2007/060255 (AGFA GRAPHICS) and EP 1790695 A (AGFA GRAPHICS).

In dispersing C.I. Pigment Blue 15:3, the use of a sulfonated Cu-phthalocyanine dispersion synergist, e.g. SOLSPERSE™ 5000 from NOVEON is preferred. Suitable dispersion synergists for yellow inkjet inks include those disclosed in EP 1790697 A (AGFA GRAPHICS).

In a preferred embodiment, the dispersion synergist includes one, two or more carboxylic acid groups and preferably no sulfonic acid groups.

Surfactants

The radiation curable compositions and inks may contain a surfactant. The surfactant(s) can be anionic, cationic, non-ionic, or zwitter-ionic and are usually added in a total quantity less than 10 wt % based on the total weight of the radiation curable composition or ink and particularly in a total less than 5 wt % based on the total weight of the radiation curable composition or ink.

Surfactants in inkjet ink reduce the surface tension of the ink in order to reduce the contact angle on the ink-receiver, i.e. to improve the wetting of the ink-receiver by the ink. On the other hand, the jettable ink must meet stringent performance criteria in order to be adequately jettable with high precision, reliability and during an extended period of time. To achieve both wetting of the ink-receiver by the ink and high jetting performance, typically, the surface tension of the ink is reduced by the addition of one or more surfactants. In the case of curable inkjet inks, however, the surface tension of the inkjet ink is not only determined by the amount and type of surfactant, but also by the polymerizable compounds, the polymeric dispersants and other additives in the ink composition.

Suitable surfactants include fluorinated surfactants, fatty acid salts, ester salts of a higher alcohol, alkylbenzene sulphonate salts, sulphosuccinate ester salts and phosphate ester salts of a higher alcohol (for example, sodium dodecylbenzenesulphonate and sodium dioctylsulphosuccinate), ethylene oxide adducts of a higher alcohol, ethylene oxide adducts of an alkylphenol, ethylene oxide adducts of a polyhydric alcohol fatty acid ester, and acetylene glycol and ethylene oxide adducts thereof (for example, polyoxyethylene nonylphenyl ether, and SURFYNOL™ 104, 104H, 440, 465 and TG available from AIR PRODUCTS & CHEMICALS INC.).

Preferred surfactants include fluoro surfactants (such as fluorinated hydrocarbons) and silicone surfactants. The silicones are typically siloxanes and can be alkoxylated, polyether modified, polyester modified, polyether modified hydroxy functional, amine modified, epoxy modified and other modifications or combinations thereof. Preferred siloxanes are polymeric, for example polydimethylsiloxanes.

Examples of useful commercial silicone surfactants are those supplied by BYK CHEMIE GMBH (including BYK™-302, 307, 310, 331, 333, 341, 345, 346, 347, 348, UV3500, UV3510 and UV3530), those supplied by TEGO CHEMIE SERVICE (including Tego RAD™ 2100, 2200N, 2250, 2300, 2500, 2600 and 2700), EBECRYL™ 1360 a polysilixone hexaacrylate from CYTEC INDUSTRIES BV and EFKA™-3000 series (including EFKA™-3232 and EFKA™-3883) from EFKA CHEMICALS B.V.

The fluorinated or silicone compound used as a surfactant is preferably a cross-linkable surfactant. Suitable polymerizable compounds having surface-active effects include, for example, polyacrylate copolymers, silicone modified acrylates, silicone modified methacrylates, acrylated siloxanes, polyether modified acrylic modified siloxanes, fluorinated acrylates, and fluorinated methacrylate. These acrylates can be mono-, di-, tri- or higher functional (meth)acrylates.

Depending upon the application a surfactant can be used with a high, low or intermediate dynamic surface tension. Silicone surfactants are generally known to have low dynamic surface tensions while fluorinated surfactants are known to have higher dynamic surface tensions.

Silicone surfactants are often preferred in curable inkjet compositions and inks, especially the reactive silicone surfactants, which are able to be polymerized together with the polymerizable compounds during the curing step.

Preparation of Pigmented Radiation Curable Compositions and Inks

The average particle size and distribution of a pigment is an important feature for inkjet inks. The inkjet ink may be prepared by precipitating or milling the pigment in the dispersion medium in the presence of the dispersant.

Mixing apparatuses may include a pressure kneader, an open kneader, a planetary mixer, a dissolver, and a Dalton Universal Mixer. Suitable milling and dispersion apparatuses are a ball mill, a pearl mill, a colloid mill, a high-speed disperser, double rollers, a bead mill, a paint conditioner, and triple rollers. The dispersions may also be prepared using ultrasonic energy.

Many different types of materials may be used as milling media, such as glasses, ceramics, metals, and plastics. In a preferred embodiment, the grinding media can comprise particles, preferably substantially spherical in shape, e.g. beads consisting essentially of a polymeric resin or yttrium stabilized zirconium oxide beads.

In the process of mixing, milling and dispersion, each process is performed with cooling to prevent build up of heat, and as much as possible under light conditions in which actinic radiation has been substantially excluded.

The inkjet ink may contain more than one pigment, and may be prepared using separate dispersions for each pigment, or alternatively several pigments may be mixed and co-milled in preparing the dispersion.

The dispersion process can be carried out in a continuous, batch or semi-batch mode.

The preferred amounts and ratios of the ingredients of the mill grind will vary widely depending upon the specific materials and the intended applications. The contents of the milling mixture comprise the mill grind and the milling media. The mill grind comprises pigment, polymeric dispersant and a liquid carrier. For inkjet inks, the pigment is usually present in the mill grind at 1 to 50 wt %, excluding the milling media. The weight ratio of pigment over polymeric dispersant is 20:1 to 1:2.

The milling time can vary widely and depends upon the pigment, mechanical means and residence conditions selected, the initial and desired final particle size, etc. In a preferred embodiment of the present invention pigment dispersions with an average particle size of less than 100 nm may be prepared.

After milling is completed, the milling media is separated from the milled particulate product (in either a dry or liquid dispersion form) using conventional separation techniques, such as by filtration, sieving through a mesh screen, and the like. Often the sieve is built into the mill, e.g. for a bead mill. The milled pigment concentrate is preferably separated from the milling media by filtration.

In general it is desirable to make inkjet inks in the form of a concentrated mill grind, which is subsequently diluted to the appropriate concentration for use in the inkjet printing system. This technique permits preparation of a greater quantity of pigmented ink from the equipment. By dilution, the inkjet ink is adjusted to the desired viscosity, surface tension, colour, hue, saturation density, and print area coverage for the particular application.

Inkjet Printing Methods

The polymerizable photoinitiator according to a preferred embodiment of the present invention is preferably used for initiating the polymerization of monomers in a radiation curable composition by using UV radiation with a wavelength larger than 360 nm.

In a preferred embodiment, the radiation curable composition including the polymerizable photoinitiator according to the present invention is used in an inkjet printing method.

The inkjet printing method preferably includes the steps of:
a) providing a radiation curable composition including a polymerisable photoinitiator according to a preferred embodiment of the present invention to an inkjet printing device;
b) depositing the radiation curable composition with the inkjet printing device on an ink-receiver; and
c) at least partially curing the radiation curable composition by using UV radiation with a wavelength larger than 360 nm.

In a preferred embodiment, the ink-receiver is a substantially non-absorbing ink-receiver. The term "substantially non-absorbing ink-jet ink-receiver" means any ink-jet ink-receiver which fulfils at least one of the following two criteria:

1) No penetration of ink into the ink-jet ink-receiver deeper than 2 μm;
2) No more than 20% of a droplet of 100 pL jetted onto the surface of the ink-jet ink-receiver disappears into the ink-jet ink-receiver in 5 seconds. If one or more coated layers are present, the dry thickness should be less than 5 μm. Standard analytical method can be used by one skilled in the art to determine whether an ink-receiver falls under either or both of the above criteria of a substantially non-absorbing ink-receiver. For example, after jetting ink on the ink-receiver surface, a slice of the ink-receiver can be taken and examined by transmission electron microscopy to determine if the penetration depth of the ink is greater than 2 μm. Further information regarding suitable analytical methods can be found in the article: DESIE, G, et al. Influence of Substrate Properties in Drop on Demand Printing. *Proceedings of Imaging Science and Technology's* 18*th International Conference on Non Impact Printing.* 2002, p. 360-365.

Inkjet Printing Devices

The radiation curable inkjet compositions and inks may be jetted by one or more print heads ejecting small droplets of ink in a controlled manner through nozzles onto an ink-receiver surface, which is moving relative to the print head(s).

A preferred print head for the inkjet printing system is a piezoelectric head. Piezoelectric inkjet printing is based on the movement of a piezoelectric ceramic transducer when a voltage is applied thereto. The application of a voltage changes the shape of the piezoelectric ceramic transducer in the print head creating a void, which is then filled with ink. When the voltage is again removed, the ceramic expands to its original shape, ejecting a drop of ink from the print head. However the inkjet printing method according to a preferred embodiment of the present invention is not restricted to piezoelectric inkjet printing. Other inkjet print heads can be used and include various types, such as a continuous type and thermal, electrostatic and acoustic drop on demand type.

The inkjet print head normally scans back and forth in a transversal direction across the moving ink-receiver surface. Often the inkjet print head does not print on the way back. Bi-directional printing is preferred for obtaining a high areal throughput. Another preferred printing method is by a "single pass printing process", which can be performed by using page wide inkjet print heads or multiple staggered inkjet print heads which cover the entire width of the ink-receiver surface. In a single pass printing process the inkjet print heads usually remain stationary and the ink-receiver surface is transported under the inkjet print heads.

Curing Devices

The radiation curable compositions and inkjet inks according to a preferred embodiment of the present invention can be cured by exposing them to actinic radiation, preferably by ultraviolet radiation.

In inkjet printing, the curing means may be arranged in combination with the print head of the inkjet printer, travelling therewith so that the curable composition is exposed to curing radiation very shortly after been jetted.

In such an arrangement it can be difficult to provide a small enough radiation source connected to and travelling with the print head, such as LED. Therefore, a static fixed radiation source may be employed, e.g. a source of curing UV-light, connected to the radiation source by means of flexible radiation conductive means such as a fiber optic bundle or an internally reflective flexible tube.

Alternatively, the actinic radiation may be supplied from a fixed source to the radiation head by an arrangement of mirrors including a mirror upon the radiation head.

The source of radiation arranged not to move with the print head, may also be an elongated radiation source extending transversely across the ink-receiver surface to be cured and adjacent the transverse path of the print head so that the subsequent rows of images formed by the print head are passed, stepwise or continually, beneath that radiation source.

Any ultraviolet light source, as long as part of the emitted light can be absorbed by the photo-initiator or photo-initiator system, may be employed as a radiation source, such as, a high or low pressure mercury lamp, a cold cathode tube, a black light, an ultraviolet LED, an ultraviolet laser, and a flash light. Of these, the preferred source is one exhibiting a relatively long wavelength UV-contribution having a dominant wavelength of 300-400 nm. Specifically, a UV-A light source is preferred due to the reduced light scattering therewith resulting in more efficient interior curing.

UV radiation is generally classed as UV-A, UV-B, and UV-C as follows:
UV-A: 400 nm to 320 nm
UV-B: 320 nm to 290 nm
UV-C: 290 nm to 100 nm.

In a preferred embodiment of the method of inkjet printing according to the present invention, the inkjet printing device contains one or more UV LEDs with a wavelength larger than 360 nm, preferably one or more UV LEDs with a wavelength larger than 380 nm, and most preferably UV LEDs with a wavelength of about 395 nm.

Furthermore, it is possible to cure the image using, consecutively or simultaneously, two light sources of differing wavelength or illuminance. For example, the first UV-source can be selected to be rich in UV-C, in particular in the range of 260 nm-200 nm. The second UV-source can then be rich in UV-A, e.g. a gallium-doped lamp, or a different lamp high in both UV-A and UV-B. The use of two UV-sources has been found to have advantages e.g. a fast curing speed and a high curing degree.

For facilitating curing, the inkjet printer often includes one or more oxygen depletion units. The oxygen depletion units place a blanket of nitrogen or other relatively inert gas (e.g. $CO_2$), with adjustable position and adjustable inert gas concentration, in order to reduce the oxygen concentration in the curing environment. Residual oxygen levels are usually maintained as low as 200 ppm, but are generally in the range of 200 ppm to 1200 ppm.

Industial Applicability

The polymerisable photoinitiator according to preferred embodiments of the present invention can be used to prepare radiation curable compositions and inks which after curing are required to have minimal extractable and volatile compounds, such as food packaging applications involving, for example, short run packaging inkjet printing or flexographic printing on packaging materials.

However, the polymerisable photoinitiator may also be used in radiation curable compositions and inks have less strict regulations on extractables and volatiles, such as e.g. billboard or poster printing, since it enhances the safety for the operator in preparing these billboards and posters.

The polymerisable photoinitiator can also be advantageously used not only in the preparation of lithographic printing plates as exemplified by US 2008008966 (FUJIFILM) or flexographic printing plates as exemplified by US 2006055761 (AGFA GRAPHICS), but also in the preparation of flexographic or lithographic radiation curing inks to be used with these printing plates as exemplified in US 2009018230 (CIBA).

EXAMPLES

Materials

All materials used in the following examples were readily available from standard sources such as ALDRICH CHEMICAL Co. (Belgium) and ACROS (Belgium) unless otherwise specified.

LEWATIT™ M600 MB is available from CLEARTECH INDUSTRIES INC. Activated LEWATIT™ M600 MB means that it received an alkaline treatment according to the following method: 25 g of LEWATIT™ M600 MB was treated with 75 mL of 1 N sodium hydroxide solution and stirred for 2 hours. The ion exchanger was isolated by filtration, washed several times with water and dried until constant weight.

SPECIAL BLACK™ 550 is a carbon black pigment available from EVONIK (DEGUSSA).

HOSTAPERM™ Blue P-BFS is a C.I. Pigment Blue 15:4 pigment from CLARIANT.

DB162 is an abbreviation used for the polymeric dispersant DISPERBYK™ 162 available from BYK CHEMIE GMBH whereof the solvent mixture of 2-methoxy-1-methylethylacetate, xylene and n-butylacetate was removed.

VEEA is 2-(2'-vinyloxyethoxy)ethylacrylate, a difunctional monomer available from NIPPON SHOKUBAI, Japan.

M600 is dipentaerythritol hexaacrylate and an abbreviation for MIRAMER™ M600 available from RAHN AG.

SC7040 is SPEEDCURE™ 7040, a polymeric co-initiator supplied by Lambson Ltd.

IC819 is IRGACURE™ 819, supplied by BASF (Ciba Specialty Chemicals)

COMPINI-1 is a polymerisable thioxanthone having the following structure:

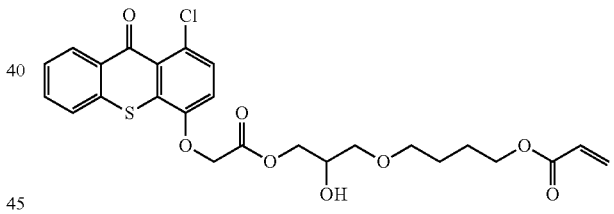

and was prepared as described below:

Step 1: synthesis of (1-chloro-9-oxo-9H-thioxanthen-4-yloxy)-acetic acid

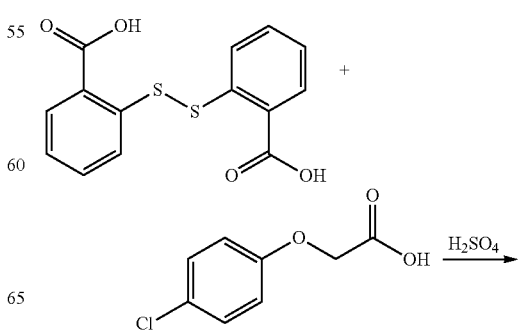

-continued

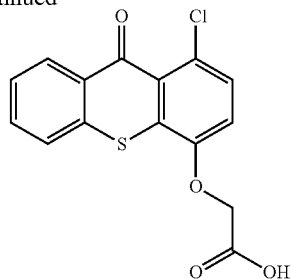

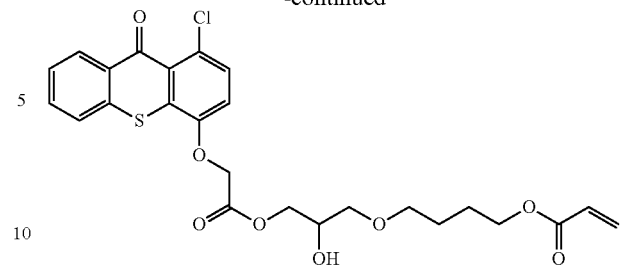

Sulfuric acid (18M) (1620 mL) was cooled to −5° C. and 2,2'-dithiosalicylic acid (165.4 g, 0.54 mol) was added, followed by the addition of 4-chlorophenoxyacetic acid (352.7 g, 1.89 mol) over 3 hours, which resulted in the formation of thick yellow/green suspension. This suspension was stirred for 1 hour at 0° C. The reaction mixture was heated at 50° C. and allowed to stir for 54 hours. After reaction, the reaction mixture was poured into ice (1300 g). After stirring for 1 hour at room temperature, the crude (1-chloro-9-oxo-9H-thioxanthen-4-yloxy)-acetic acid was isolated by filtration. The crude (1-chloro-9-oxo-9H-thioxanthen-4-yloxy)-acetic acid was recrystallized from acetonitrile (3000 mL). (1-chloro-9-oxo-9H-thioxanthen-4-yloxy)-acetic acid was isolated by filtration, yielding 186.3 g (53.8%) (1-chloro-9-oxo-9H-thioxanthen-4-yloxy)-acetic acid.

Step 2: synthesis of acrylic acid 4-{3-[2-(1-chloro-9-oxo-9H-thioxanthen-4-yloxy)-acetoxy]-2-hydroxy-propoxy}-butyl ester

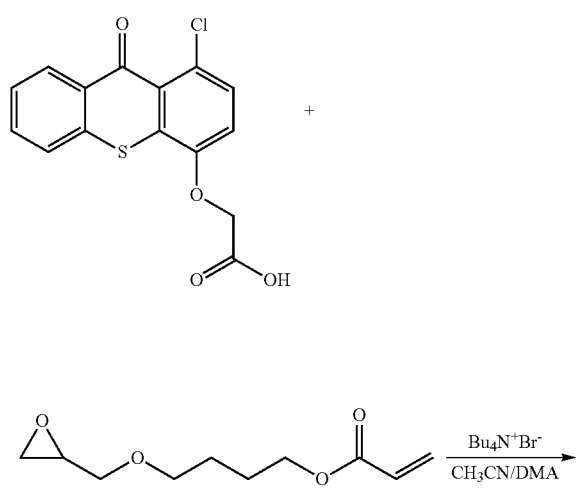

A reaction mixture containing (1-chloro-9-oxo-9H-thioxanthen-4-yloxy)-acetic acid (28.9 g, 0.09 mol), acetonitrile (345 mL), dimethylacetamide (240 ml), tetrabutylammonium bromide (2.9 g, 9 mmol), 2,6-di-tert-butyl-4-methylphenol (0.2 g, 0.9 mmol) and 4-hydroxybutylacrylate glycidylether (18.0 g, 0.09 mol) was heated to reflux. The mixture was allowed to stir at reflux temperature for 24 hours. The reaction mixture was cooled to room temperature and the solvent was evaporated under reduced pressure. The residual oil was dissolved in dichloromethane (400 mL) and extracted 3 times with a mixture of an aqueous solution of sodium hydroxide (1N) (200 mL) and distilled water (200 mL). The organic layer was isolated and dried over MgSO$_4$. The solvent was evaporated to yield 15.7 g of a brown oil. Acrylic acid 4-{3-[2-(1-chloro-9-oxo-9H-thioxanthen-4-yloxy)-acetoxy]-2-hydroxy-propoxy}-butyl ester was purified on a Merck Super Vario Prep column using dichloromethane/ethyl acetate (75/25) as eluent, yielding 13.85 g of a yellow oil.

BYK™ UV3510 is a polyethermodified polydimethylsiloxane wetting agent available from BYK CHEMIE GMBH GENORAD™ 16 is a polymerization inhibitor from RAHN AG.

PGA-paper is a double sided PE paper, containing 9% TiO$_2$ in the PE layer.

PET100 is a 100 μm unsubbed PET substrate with on the backside an antiblocking layer with antistatic properties available from AGFA-GEVAERT as P100C PLAIN/ABAS.

IRGACURE™ 127 is a photoinitiator having the following structure:

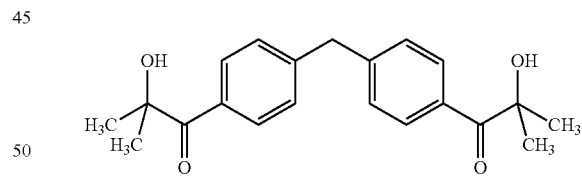

and was supplied by BASF (Ciba Specialty Chemicals).

Type I is a polymerisable Norrish type I initiator having the following structure:

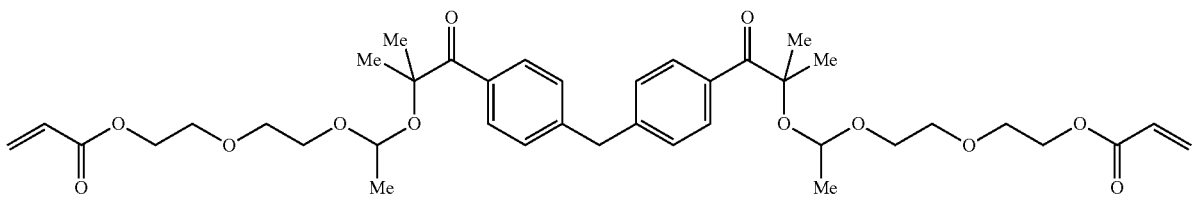 [SMILES: C=CC(=O)OCCOCCOC(C)OC(C)(C)C(=O)c1ccc(Cc2ccc(C(=O)C(C)(C)OC(C)OCCOCCOC(=O)C=C)cc2)cc1]

which was prepared as described below:

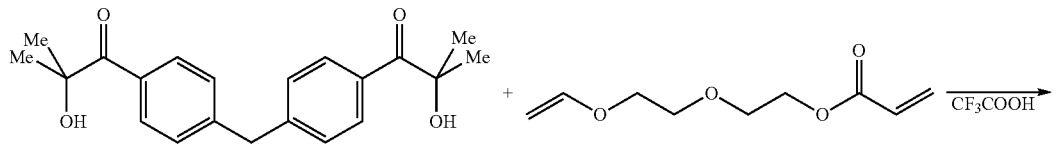

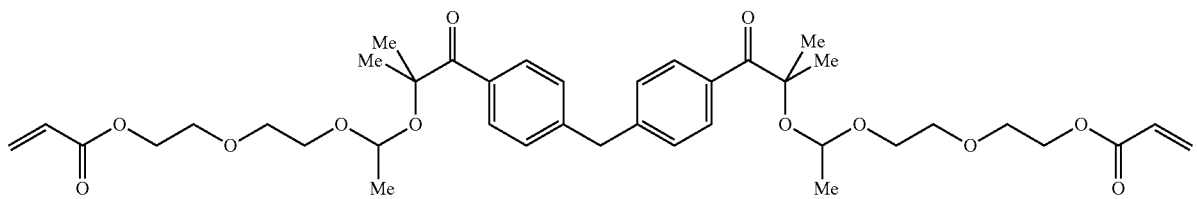

100 g (0.294 mol) IRGACURE™ 127 was dissolved in 500 mL ethyl acetate. 186 g (1 mol) 2-(2'-vinyloxyethoxy)ethylacrylate, 0.7 g (0.458 ml, 5.9 mmol) trifluoro acetic acid and 1.3 g (5.9 mmol) BHT were added. The mixture was heated to 70° C. for 16 hours. The reaction mixture was allowed to cool down to room temperature and 100 g activated LEWATIT™ M600 MB was added. The reaction mixture was stirred for 1 hour. LEWATIT™ M600 MB was removed by filtration. The ethyl acetate was evaporated under reduced pressure, yielding a 63 w % solution of Type I in 2-(2'-vinyloxyethoxy)ethylacrylate, which was used as such in the comparative and inventive radiation curable compositions.

PCI-1 is a polymerisable co initiator having the following structure:

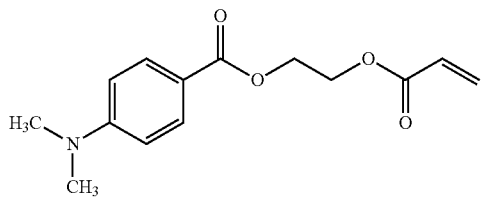 [SMILES: C=CC(=O)OCCOC(=O)c1ccc(N(C)C)cc1]

and was prepared as disclosed in example 1 of EP 2033949 A (AGFA GRAPHICS).

COMPINI-2 is acrylic-acid 2-{2-[1-(1-chloro-9-oxo-9H-thioxanthen-4-yloxy)-ethoxy]-ethoxy}-ethyl ester, a polymerisable thioxanthone, having the following structure:

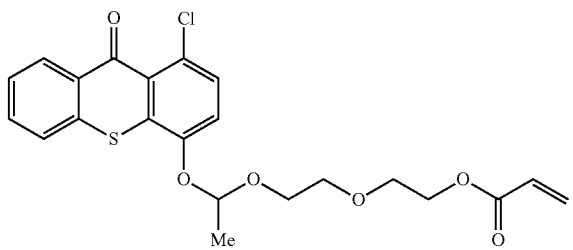 [SMILES: C=CC(=O)OCCOCCOC(C)Oc1ccc(Cl)c2c(=O)c3ccccc3sc12]

and was prepared as follows:

Step 1: synthesis of
1-Chloro-4-hydroxy-thioxanthen-9-one

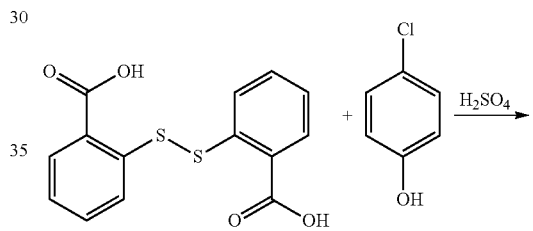

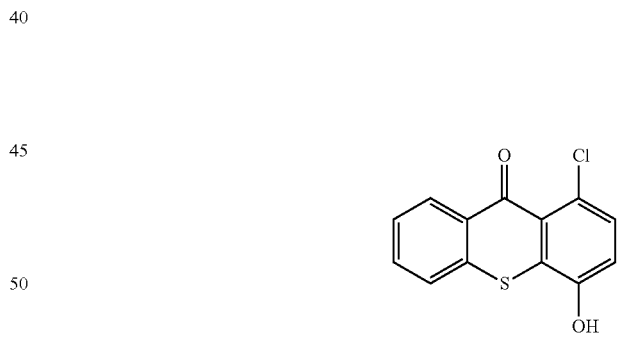

2,2'-dithiosalicylic acid (84.4 g, 0.27 mol) was added to sulfuric acid (18M) (300 mL). The suspension was cooled to −5° C. and 4-chlorophenol (120.2 g, 0.94 mol) was added and the mixture was slowly brought to room temperature. The reaction mixture was heated to 60° C. and allowed to stir for 15 hours and another 6 hours at 70° C. After reaction, the reaction mixture was poured into a mixture of ice (500 g) and distilled water (200 ml). The crude 1-chloro-4-hydroxy-hioxanthen-9-one precipitated from the medium and was isolated by filtration. The crude 1-chloro-4-hydroxy-hioxanthen-9-one was dissolved in water, using an aqueous solution of potassium hydroxide (1.5 N) (3.5 L). The mixture was acidified to pH=2.4 with an aqueous solution of hydrochloric acid (12M). 1-chloro-4-hydroxy-hioxanthen-9-one was isolated by filtration and dried to yield 140 g (99%) of 1-Chloro-4-hydroxy-hioxanthen-9-one.

Step 2: synthesis of acrylic-acid 2-{2-[1-(1-chloro-9-oxo-9H-thioxanthen-4-yloxy)-ethoxy]-ethoxy}-ethyl ester

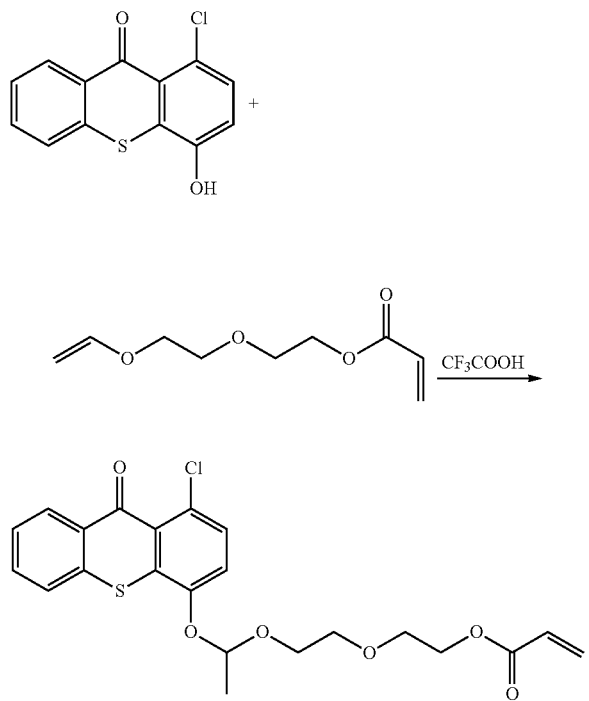

1-Chloro-4-hydroxy-hioxanthen-9-one (6.2 g, 24 mmol), 2,6-di-tert-butyl-4-methylphenol (0.1 g, 0.47 mmol) and trifluoroacetic acid (0.053 g=34.9 µL, 0.47 mmol) were added to 2-(2'-vinyloxyethoxy)ethylacrylate (42.4 g). This solution was heated at 60° C. and stirred for 2.5 hours. After cooling down to room temperature, activated LEWATIT™ M600 MB (8.2 g) was added and the mixture was stirred for 1 hour. LEWATIT™ M600 MB was removed by filtration to yield a 25 w % solution of COMPINI-2.

COMPINI-3 is acrylic acid 2-(2-{1-[2-{1-[2-(2-acryloyloxy-ethoxy)-ethoxy]-ethoxy}-3-(1-chloro-9-oxo-9H-thioxanthen-4-yloxy)-propoxy]-ethoxy}-ethoxy)-ethyl ester, a polymerisable thioxanthone, having the following structure:

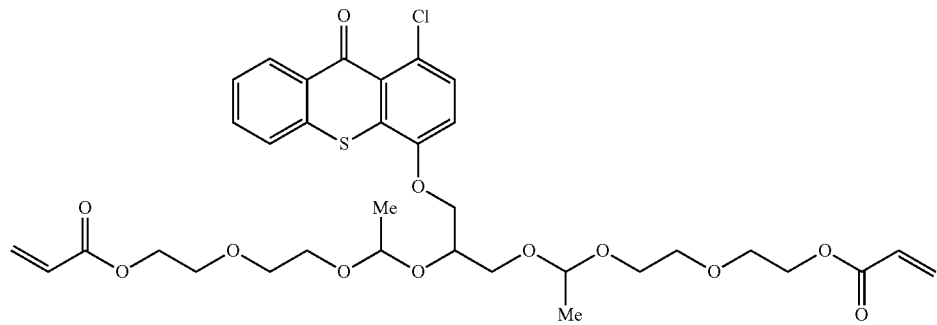

and was prepared as follows:

Step 1: synthesis of 1-Chloro-4-(2,3-dihydroxy-propoxy)-thioxanthen-9-one

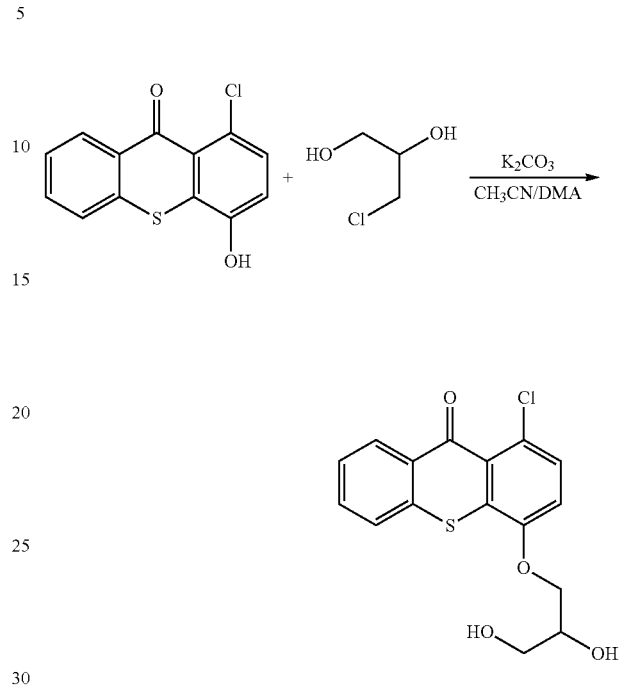

1-Chloro-4-hydroxy-hioxanthen-9-one was prepared as described above. To a solution of 1-chloro-4-hydroxy-hioxanthen-9-one (15 g, 0.057 mol) in acetonitrile (200 mL) and dimethylacetamide (50 mL) at 70° C., potassium carbonate (34.7 g, 0.251 mol) was added followed by the addition of 3-chloro-1,2-propanediol (15.1 g, 0.137 mol). The reaction mixture was heated to reflux (88° C.) and was allow to stir at this temperature for 24 hours. The reaction mixture was cooled to room temperature and the solvent was evaporated under reduced pressure. The residual oil was dissolved in methyl-tert-butylether (300 mL) and extracted with a mixture of an aqueous solution of sodium hydroxide (1N) (50 mL) and distilled water (300 ml). The organic layer was isolated, dried over MgSO$_4$, and evaporated under reduced pressure to yield 20 g of the crude 1-chloro-4-(2,3-dihydroxy-propoxy)-thioxanthen-9-one as a viscous an oil. The crude 1-chloro-4-(2,3-dihydroxy-propoxy)-thioxanthen-9-one was purified on a Prochrom LC80 using methanol/0.2 M ammonium acetate (70/30) as eluent, to yield 8.45 g of 1-chloro-4-(2,3-dihydroxy-propoxy)-thioxanthen-9-one.

Step 2: synthesis of acrylic acid 2-(2-{1-[2-{1-[2-(2-acryloyloxy-ethoxy)-ethoxy]-ethoxy}-3-(1-chloro-9-oxo-9H-thioxanthen-4-yloxy)-propoxy]-ethoxy}-ethoxy)-ethyl ester

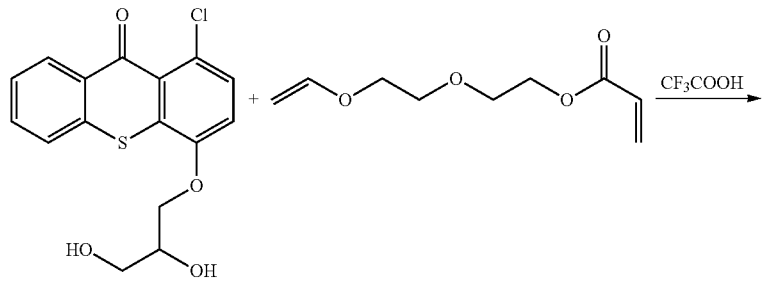

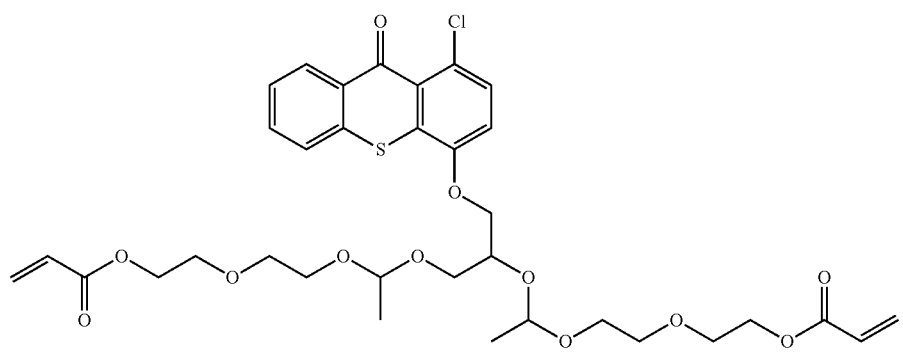

1-Chloro-4-(2,3-dihydroxy-propoxy)-thioxanthen-9-one (2 g, 6 mmol), 2,6-di-tert-butyl-4-methylphenol (0.013 g, 0.06 mmol) and trifluoroacetic acid (7 mg=4.6 μl, 0.06 mmol) were dissolved in VEEA (16.9 g). The reaction mixture was heated at 70° C. and stirred for 6 hours. After cooling down to room temperature, activated LEWATIT™ M600 MB (5.0 g) was added and stirred for 1 hour. LEWATIT™ M600 MB was removed by filtration, yielding a 25 w % solution of acrylic acid 2-(2-{1-[2-{1-[2-(2-acryloyloxy-ethoxy)-ethoxy]-ethoxy}-3-(1-chloro-9-oxo-9H-thioxanthen-4-yloxy)-propoxy]-ethoxy}-ethoxy)-ethyl ester in 2-(2'-vinyloxyethoxy) ethylacrylate.

Measurement Methods

1. Curing speed D-Bulb

A radiation curable composition was coated on a PET100 substrate using a bar coater and a 10 μm wired bar. The coated sample was fully cured using a Fusion DRSE-120 conveyer, equipped with a Fusion VPS/1600 lamp (D-bulb), which transported the sample under the UV-lamp on a conveyer belt at a speed of 20 m/min. The maximum output of the lamp was 1.05 J/cm² and a peak intensity of 5.6 W/cm². The percentage of the maximum output of the lamp was taken as a measure for curing speed, the lower the number the higher the curing speed. A sample was considered as fully cured at the moment scratching with a Q-tip caused no visual damage.

2. Curing Speed LED

A radiation curable composition was coated on PGA-paper, using a bar coater and a 10 μm wired bar. The coated sample was mounted on a belt, transporting the sample under a Phoseon 4W 395 nm LED at a speed of 5 m/min and at a distance of 4.5 mm from the LED. The curing speed was evaluated based on visual damage when using a Q-tip, resulting in a score varying from 0 for no visual damage at all up to 5 for complete wiping away the coating. A score of 0 and 1 is considered as good to acceptable. A score from 3 to 5 is considered as completely unacceptable.

3. Average Particle Size

The particle size of pigment particles in a pigment dispersion was determined by photon correlation spectroscopy at a wavelength of 633 nm with a 4 mW HeNe laser on a diluted sample of the pigment dispersion. The particle size analyzer used was a MALVERN™ nano-S available from Goffin-Meyvis.

The sample was prepared by addition of one drop of pigment dispersion to a cuvette containing 1.5 mL ethyl acetate and mixed until a homogenous sample was obtained. The measured particle size is the average value of 3 consecutive measurements consisting of 6 runs of 20 seconds.

Example 1

This example illustrates how the polymerizable photoinitiators according to a preferred embodiment of the present invention can be prepared.

Example 1a

The polymerizable photoinitiator FITX-1 (acrylic acid 2-{2-[1-(1-fluoro-9-oxo-9H-thioxanthen-4-yloxy)-ethoxy]-ethoxy}-ethyl ester) was prepared according to the following synthesis method:

Step 1: synthesis of 1-fluoro-4-hydroxy-thioxanthen-9-one

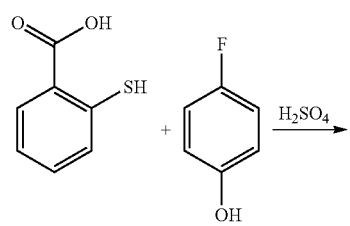

Thiosalicylic acid (5.1 g, 0.033 mol) was added in portions to 20 mL sulfuric acid (18M), which causes the temperature to rise to 30° C. At this temperature 4-fluorophenol (11.2 g, 0.10 mol) was added in portions to the suspension. The mixture was heated to 80° C. and stirred for 12 hours. After the reaction, the reaction mixture was poured into ice (150 g). 1-fluoro-4-hydroxy-thioxanthen-9-one precipitated from the medium and was isolated by filtration. The crude 1-fluoro-4-hydroxy-thioxanthen-9-one was dissolved in water at pH=14 using an aqueous solution of potassium hydroxide and stirred for 60 minutes. The mixture was acidified to pH=4 using acetic acid. 1-fluoro-4-hydroxy-thioxanthen-9-one was isolated by filtration and dried to obtain 5.5 g of 1-fluoro-4-hydroxy-thioxanthen-9-one.

Step 2: synthesis of acrylic acid 2-{2-[1-(1-fluoro-9-oxo-9H-thioxanthen-4-yloxy)-ethoxy]-ethoxy}-ethyl ester

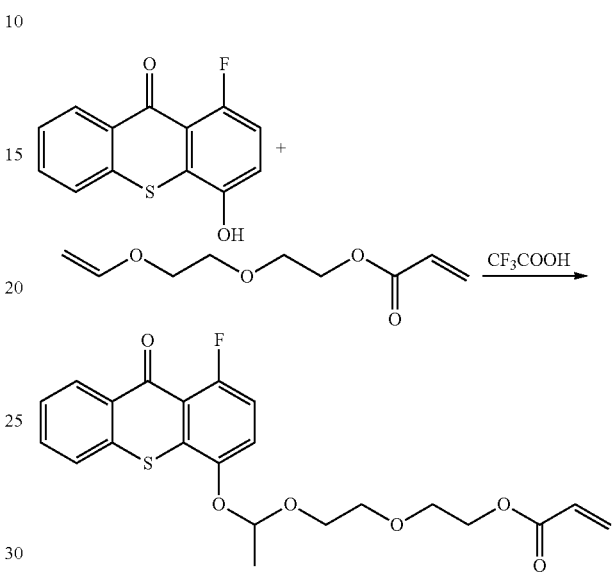

1-fluoro-4-hydroxy-thioxanthen-9-one (2.5 g, 0.01 mol), 2,6-di-tert-butyl-4-methylphenol (0.07 g, 0.32 mmol) and trifluoroacetic acid (0.1 g=92.4 µL, 1.2 mmol) were added to 2-(2'-vinyloxyethoxy)ethylacrylate (27.6 g). The mixture was heated to 70° C. and stirred for 4 hours. After cooling down to room temperature, activated Lewatit M600 MB (10 g) was added and stirred for 1 hour. After filtration, a 15 w % solution of acrylic acid 2-{2-[1-(1-fluoro-9-oxo-9H-thioxanthen-4-yloxy)-ethoxy]-ethoxy}-ethyl ester in 2-(2'-vinyloxyethoxy)ethylacrylate was obtained, which was directly used in the radiation curable compositions according to a preferred embodiment of the present invention.

Example 1b

The polymerizable photoinitiator FITX-2 (acrylic acid 2-acryloyloxy-3-(1-fluoro-9-oxo-9H-thioxanthen-4-yloxy)-propyl ester) was prepared according to the following synthesis method:

Step 1: synthesis of 4-(2,3-dihydroxy-propoxy)-1-fluoro-thioxanthen-9-one

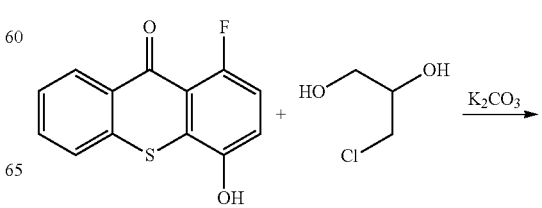

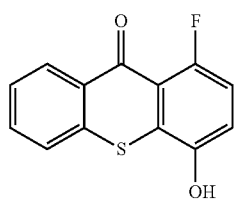

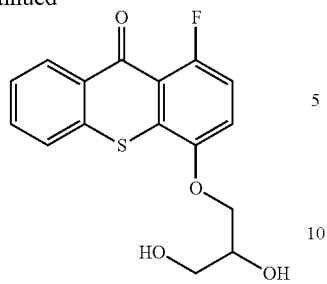

The reactant 1-fluoro-4-hydroxy-thioxanthen-9-one was prepared as described above in Example 1a. To a suspension of 1-fluoro-4-hydroxy-9H-thioxanthen-9-on (92%) (306 g, 1.14 mol) in acetonitrile (3500 mL), potassium carbonate (464 g, 3.36 mol) was added while stirring vigorously. 3-Chloro-1,2-propanediol (371 g, 3.36 mol) was added drop wise over 30 minutes. The reaction mixture was heated to reflux and allowed to stir for 24 hours. The mixture was filtered and the residue was washed with warm acetonitrile (500 mL) (70° C.). The filtrate was evaporated under reduced pressure. The residual solid was treated with a mixture of methyl-tert-butylether (400 mL) and acetone (40 ml) and stirred for about an hour. The crude 4-(2,3-dihydroxy-propoxy)-1-fluoro-thioxanthen-9-one was isolated by filtration and dried. The crude 4-(2,3-dihydroxy-propoxy)-1-fluoro-thioxanthen-9-one was treated twice with 1000 mL water at 60° C., isolated by filtration and dried.

Step 2: synthesis of acrylic acid 2-acryloyloxy-3-(1-fluoro-9-oxo-9H-thioxanthen-4-yloxy)-propyl ester

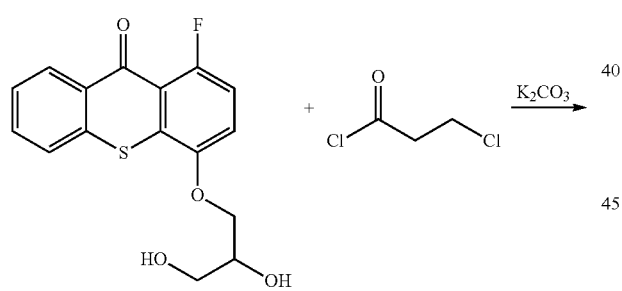

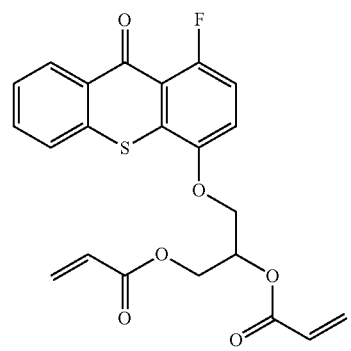

4-(2,3-dihydroxy-propoxy)-1-fluoro-thioxanthen-9-one (2.9 g, 9 mmol), 3-chloropropionyl chloride (9.5 g, 75 mmol), potassium carbonate (10.4 g, 75 mmol) and 2,6-di-tert-butyl-4-methylphenol (0.1 g, 0.00045 mol) were added to acetonitrile (35 mL). The reaction mixture was heated at 81° C. and stirred for 6 hours. After cooling down to room temperature, dichloromethane (200 mL) was added and the reaction mixture was extracted with distilled water (200 mL). The organic layer was separated, dried over MgSO$_4$ and evaporated under reduced pressure. The product was purified on a Prochrom LC 80 Column using dichloromethane/ethyl acetate (98/2) as eluent and Kromasil Si60A 10 µm as packing material, to yield 1.2 g of acrylic acid 2-acryloyloxy-3-(1-fluoro-9-oxo-9H-thioxanthen-4-yloxy)-propyl ester.

Example 1c

The polymerizable photoinitiator FITX-3 (acrylic acid 2-(2-{1-[2-(2-acryloyloxy-ethoxy)-ethoxy]-ethoxy}-3-(1-fluoro-9-oxo-9H-thioxanthen-4-yloxy)-propoxy)ethoxy}-ethylester) was prepared according to the following synthesis method:

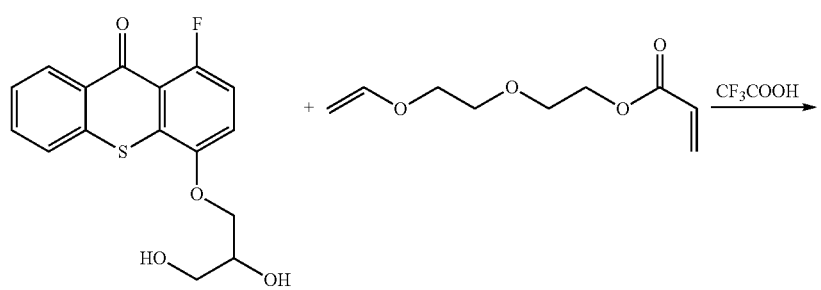

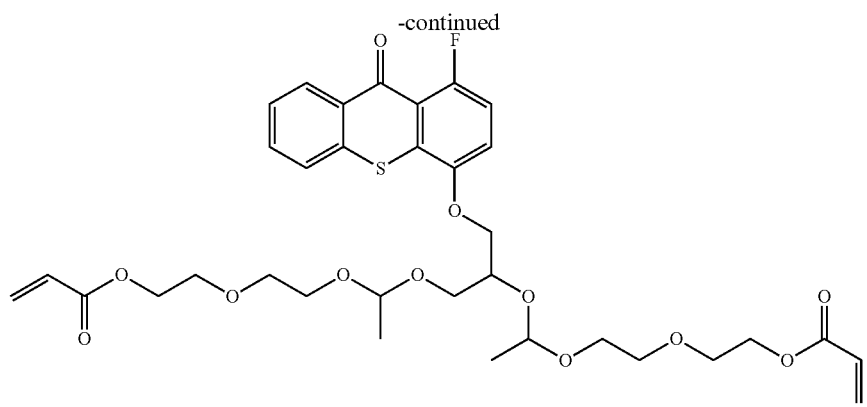

4-(2,3-dihydroxy-propoxy)-1-fluoro-thioxanthen-9-one was prepared as described in Example 1b. 4-(2,3-dihydroxy-propoxy)-1-fluoro-thioxanthen-9-one (97.8%) (117.9 g, 0.36 mol), 2,6-di-tert-butyl-4-methylphenol (1.6 g, 7.2 mol) and trifluoroacetic acid ((1.64 g=1.07 mL, 14.4 mol) were added to 2-(2'-vinyloxyethoxy)ethylacrylate (998 g). This solution was heated at 70° C. and stirred for 6 hours. After cooling down to room temperature, activated LEWATIT™ M600 MB (16.4 g) was added and stirred for 1 hour. After removal of LEWATIT™ M600 MB by filtration, a 25 w % solution of acrylic acid 2-(2-{1-[2-(2-acryloyloxy-ethoxy)-ethoxy]-ethoxy}-3-(1-fluoro-9-oxo-9H-thioxanthen-4-yloxy)-propoxy)ethoxy}-ethylester in 2-(2'-vinyloxyethoxy)ethylacrylate was obtained, which was directly used in radiation curable compositions according to a preferred embodiment of the present invention.

Example 1d

The polymerizable photoinitiator FITX-4 (acrylic acid 4-{3-[2-(1-fluoro-9-oxo-9H-thioxanthen-4-yloxy)-acetoxy]-2-hydroxy-propoxy}-butyl ester) was prepared according to the following synthesis method:

Step 1: synthesis of 1-fluoro-9-oxo-9H-thioxanthen-4-yloxy)-acetic acid

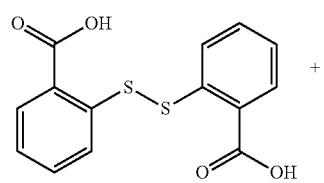

+

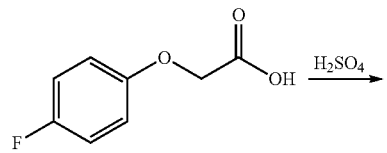

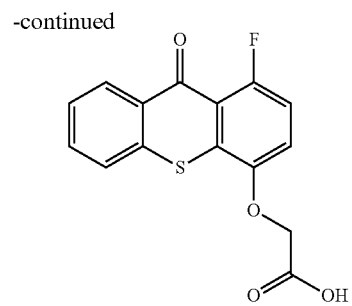

To 60 mL sulfuric acid (18M), cooled to −5° C., 2,2'-dithiosalicylic acid (6.1 g, 0.02 mol) was added in portions, followed by the addition of 4-fluorophenoxyacetic acid (11.9 g, 0.07 mol), which resulted in the formation of thick yellow suspension. The reaction mixture is heated to 60° C. and allowed to stir for 6 hours. After the reaction, the reaction mixture was poured into ice (300 g) and distilled water (100 mL). The crude (1-fluoro-9-oxo-9H-thioxanthen-4-yloxy)-acetic acid was isolated by filtration. The crude (1-fluoro-9-oxo-9H-thioxanthen-4-yloxy)-acetic acid was recrystallized from 250 mL acetonitrile. (1-fluoro-9-oxo-9H-thioxanthen-4-yloxy)-acetic acid was isolated by filtration and dried yielding 4.5 g (38.9%) of (1-fluoro-9-oxo-9H-thioxanthen-4-yloxy)-acetic acid.

Step 2: synthesis of acrylic acid 4-{3-[2-(1-fluoro-9-oxo-9H-thioxanthen-4-yloxy)-acetoxy]-2-hydroxy-propoxy}-butyl ester

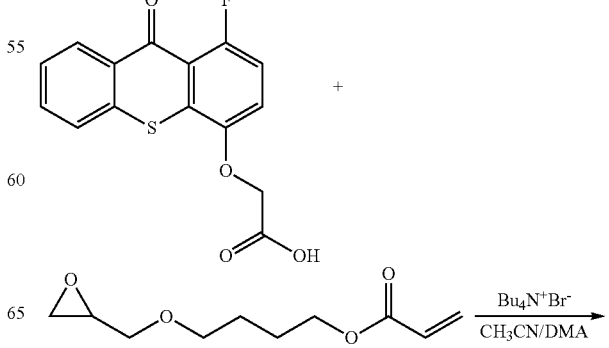

-continued

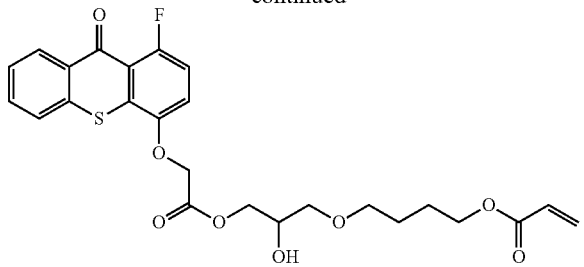

A reaction mixture containing (1-fluoro-9-oxo-9H-thioxanthen-4-yloxy)-acetic acid (4.0 g, 13 mmol), acetonitrile (65 mL), dimethylacetamide (30 ml), tetrabutylammonium bromide (0.4 g, 1.3 mmol), 2,6-di-tert-butyl-4-methylphenol (0.03 g, 0.13 mmol) and 4-hydroxybutylacrylate glycidylether (2.6 g, 13 mmol) was heated to reflux (94° C.). The mixture was allowed to stir at reflux temperature for 24 hours. The solvent was removed under reduced pressure. The residual oil was dissolved in dichloromethane (100 mL) and extracted with a mixture of distilled water (50 ml) and an aqueous solution of sodium hydroxide 1N (50 mL). The organic layer was isolated, dried over $MgSO_4$. Evaporation of the solvent under reduced pressure yielded 7.5 g of the crude acrylic acid 4-{3-[2-(1-fluoro-9-oxo-9H-thioxanthen-4-yloxy)-acetoxy]-2-hydroxy-propoxy}-butyl ester. The product was purified on a Merck Super Vario Prep Column using dichloromethane/ethyl acetate (75/25) as eluent, yielding 2.8 g of 4-{3-[2-(1-fluoro-9-oxo-9H-thioxanthen-4-yloxy)-acetoxy]-2-hydroxy-propoxy}-butyl ester as a yellow oil.

Example 2

This example illustrates the high curing speed of radiation curable compositions according to a preferred embodiment of the present invention for both UV-LED and mercury lamp radiation.

Preparation of Radiation Curable Compositions

First a concentrated pigment dispersion DISP1 was prepared. A 30 wt % solution of DB162 in 2-(2'-vinyloxyethoxy)ethylacrylate was prepared. 1 w/w % GENORAD™ 16 was added. 99.27 g Special Black 550 and 35.73 g HOSTAPERM™ Blue P-BFS were added to a mixture of 306 g 2-(2'-vinyloxyethoxy)ethylacrylate, 450 g of the DB162 solution and 9 g GENORAD™ 16, while stirring with a DISPERLUX dispenser. Stirring was continued for 30 minutes. The vessel was connected to a Netzsch Mini-Zeta filled for 50% with 0.4 mm yttrium stabilized zirconia beads ("high wear resistant zirconia grinding media" from TOSOH Co.). The mixture was circulated over the mill for 4 hours at a flow rate of 150 mL/min and a rotation speed in the mill of about 10.4 m/s. During the complete milling procedure the content in the mill was cooled to a temperature of 28° C. After milling, the dispersion DISP-1 was discharged into a 2 L-vessel. The resulting concentrated pigment dispersion DISP-1 according to Table 6 exhibited an average particle size of 102 nm.

TABLE 6

| Component | wt % |
|---|---|
| SPECIAL BLACK ™ 550 | 11 |
| HOSTAPERM ™ Blue P-BFS | 4 |
| DB162 | 15 |
| GENORAD ™ 16 | 1 |
| VEEA | 69 |

The comparative radiation curable composition COMP-1 and inventive radiation curable compositions INV-1 to INV-4 were prepared according to Table 7. The weight % (wt %) was based on the total weight of the radiation curable compositions.

TABLE 7

| wt % of | COMP-1 | INV-1 | INV-2 | INV-3 | INV-4 |
|---|---|---|---|---|---|
| VEEA | 59 | 31 | 59 | 44 | 59 |
| M600 | 6 | 6 | 6 | 6 | 6 |
| SC7040 | 5 | 5 | 5 | 5 | 5 |
| IC819 | 3 | 3 | 3 | 3 | 3 |
| COMPINI-1 | 5 | — | — | — | — |
| FITX-1 (15 w % in VEEA) | — | 33 | — | — | — |
| FITX-2 | — | — | 5 | — | — |
| FITX-3 (25 w % in VEEA) | — | — | — | 20 | — |
| FITX-4 | — | — | — | — | 5 |
| DISP1 | 20 | 20 | 20 | 20 | 20 |
| BYK ™ UV3510 | 1 | 1 | 1 | 1 | 1 |
| GENORAD ™ 16 | 1 | 1 | 1 | 1 | 1 |

Evaluation and Results

The viscosity of comparative radiation curable composition COMP-1 and inventive radiation curable compositions INV-1 to INV-4 was measured, using a Brookfield DV-II+ viscometer at 45° C. at 12 rotations per minute (which corresponds to a shear rate of 90 $s^{-1}$). The measured viscosities are given in Table 8.

TABLE 8

| Radiation curable composition | Viscosity (mPa · s) |
|---|---|
| COMP-1 | 6.5 |
| INV-1 | 6.4 |
| INV-2 | 6.7 |
| INV-3 | 6.6 |
| INV-4 | 6.0 |

From Table 8 it should be clear that all radiation curable compositions have a viscosity suitable for short run packaging inkjet printing.

The curing speed for mercury lamp exposure and LED exposure of the comparative radiation curable composition COMP-1 and inventive radiation curable compositions INV-1 to INV-4 was evaluated. The results for the evaluations of the curing speed are summarized in Table 9.

TABLE 9

| Radiation curable composition | Curing speed D-bulb | Curing speed LED |
|---|---|---|
| COMP-1 | 55% | 1 |
| INV-1 | 55% | 1 |
| INV-2 | 45% | 0 |
| INV-3 | 50% | 0 |
| INV-4 | 60% | 1 |

The radiation curable compositions according to preferred embodiments of the present invention exhibited a high curing speed both for mercury lamp exposure and LED exposure. It can be seen that high curing speed is especially observed for the radiation curable compositions INV-2 and INV-3 containing a polymerisable photoinitiator containing more than one polymerizable group.

Example 3

This example illustrates the reduced formation of migratable degradation products after curing the radiation curable compositions according to a preferred embodiment of the present invention.

Preparation of Radiation Curable Compositions

The comparative radiation curable compositions COMP-2 and COMP-3 and inventive radiation curable compositions INV-5 and INV-6 were prepared according to Table 10. The weight % (wt %) was based on the total weight of the radiation curable compositions.

TABLE 10

| wt % of | COMP-2 | COMP-3 | INV-5 | INV-6 |
|---|---|---|---|---|
| VEEA | 45 | 45 | 32 | 45 |
| M600 | 20 | 20 | 20 | 20 |
| Type I | 9 | 9 | 9 | 9 |
| PCI-1 | 5 | 5 | 5 | 5 |
| COMPINI-2 (25 w % in VEEA) | 20 | — | — | — |
| COMPINI-3 (25 w % in VEEA) | — | 20 | — | — |
| FITX-1 (15 w % in VEEA) | — | — | 33 | — |
| FITX-3 (25 w % in VEEA) | — | — | — | 20 |
| Dibutyl phthalate | 1 | 1 | 1 | 1 |

Evaluation and Results

Viscosity

The viscosity of the radiation curable compositions COMP-2, COMP-3, INV-5 and INV-6 was measured using a Brookfield DV-II+ viscometer at 25° C. at 6 RPM and were found to be in the range of 17 to 18 mPa·s, making them suitable for short run packaging inkjet printing.

Curing

The free radical curable compositions COMP-2, COMP-3, INV-5 and INV-6 were coated on a PET100 substrate using a bar coater and a 10 μm wired bar. Each coated sample was cured using a Fusion DRSE-120 conveyer, equipped with a Fusion VPS/1600 lamp (D-bulb), which transported the samples under the UV-lamp on a conveyer belt at a speed of 10 m/min. The lamp was used at its maximum output.

The Determination of the Extractable Residues

Two samples of 7.068 $cm^2$ of COMP-2, COMP-3, INV-5 and INV-6 were put into a 50 ml beaker and extracted with 4.5 mL acetonitrile, using ultrasound for 30 minutes. The extract was transferred into a 5 mL volumetric flask. The samples were rinsed twice with a small amount of acetonitrile and the rinsing solvent was transferred into the 5 mL volumetric flask until the volume was adjusted to 5 mL. The solution was thoroughly mixed and filtered over a 0.45 μm filter. 10 μL of each sample was injected on the HPLC.

The chromatographic method used an ALLTIME™ C18 5 μm column (150×3.2 mm) supplied by Alltech. A flow rate of 0.5 mL/min was used at a temperature of 40° C. A DAD detector at 291 nm was used to detect the extracted initiators and the co-initiator. The HPLC-method used for all samples had an applied gradient with an end run=38 min as given by Table 11.

TABLE 11

| Time (min) | % eluent A | % eluent B | % eluent C | % eluent D |
|---|---|---|---|---|
| 0 | 70 | 30 | 0 | 0 |
| 6 | 70 | 30 | 0 | 0 |
| 11 | 0 | 100 | 0 | 0 |
| 20 | 0 | 100 | 0 | 0 |
| 21 | 0 | 0 | 100 | 0 |
| 24 | 0 | 0 | 100 | 0 |
| 25 | 0 | 0 | 0 | 100 |
| 30 | 0 | 0 | 0 | 100 |
| 31 | 70 | 30 | 0 | 0 |
| 38 | 70 | 30 | 0 | 0 | wherein

Eluent A: $H_2O$+0.02M $KH_2PO_4$ pH=2.5 using $H_3PO_4$

Eluent B: $H_2O$+0.02M $KH_2PO_4$ pH=2.5 using $H_3PO_4$/$CH_3CN$ [40/60] (v/v)

Eluent C: $H_2O$/$CH_3CN$ [40/60] (v/v)

Eluent D: $H_2O$/$CH_3CN$ [10/90] (v/v).

The HPLC-analysis of the comparative radiation curable compositions COMP-2 and COMP-3 revealed the formation of considerable amounts of degradation products. High concentrations of one specific compound, not corresponding to one of the initial components of the compositions, were found. This compound was identified as IRGACURE™ 127. IRGACURE™ 127 was quantified in both the comparative and the inventive radiation curable compositions. The results are summarized in Table 12.

TABLE 12

| Radiation curable composition | Extracted amount of IRGACURE ™ 127 (mg/$m^2$) |
|---|---|
| COMP-2 | 180 |
| COMP-3 | 101 |
| INV-5 | <2 (if present) |
| INV-6 | <2 (if present) |

From Table 12, it becomes apparent that curing of the radiation curable compositions according to preferred embodiments of the present invention results in the formation of low amounts of degradation products, while the corresponding comparative compositions including the corresponding 1-chloro-4-alkoxy-thioxanthen-9-one derivatives result in the formation of an unacceptable level of migratable degradation products.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A polymerizable photoinitiator according to Formula (I):

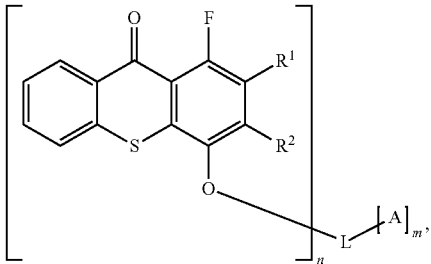

Formula (I)

wherein
- $R^1$ and $R^2$ are independently selected from the group consisting of hydrogen, a substituted or unsubstituted alkyl group, a substituted or unsubstituted alkenyl group, a substituted or unsubstituted alkynyl group, a substituted or unsubstituted aralkyl group, a substituted or unsubstituted alkaryl group, a substituted or unsubstituted aryl or heteroaryl group, a halogen, an ether group, a thioether group, an aldehyde group, a ketone group, an ester group, an amide group, an amine, and a nitro group;
- $R^1$ and $R^2$ may represent the necessary atoms to form a five to eight membered ring;
- L represents an n+m-valent linking group including 1 to 30 carbon atoms;
- A represents a radically polymerizable group selected from the group consisting of an acrylate group, a methacrylate group, a styrene group, an acryl amide group, a methacryl amide group, a maleate group, a fumarate group, an itaconate group, a vinyl ether group, an allyl ether group, a vinyl ester group, and an allyl ester group; and
- n and m independently represent an integer from 1 to 5.

2. The polymerizable photoinitiator according to claim 1, wherein $R^1$ and $R^2$ both represent hydrogen.

3. A polymerizable photoinitiator according to Formula (I):

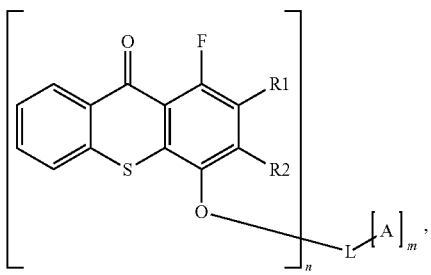

Formula (I)

wherein
- $R^1$ and $R^2$ are independently selected from the group consisting of hydrogen, a substituted or unsubstituted alkyl group, a substituted or unsubstituted alkenyl group, a substituted or unsubstituted alkynyl group, a substituted or unsubstituted aralkyl group, a substituted or unsubstituted alkaryl group, a substituted or unsubstituted aryl or heteroaryl group, a halogen, an ether group, a thioether group, an aldehyde group, a ketone group, an ester group, an amide group, an amine, and a nitro group;
- $R^1$ and $R^2$ may represent the necessary atoms to form a five to eight membered ring;
- L represents an n+m-valent linking group including 1 to 30 carbon atoms;
- A represents a radically polymerizable group selected from the group consisting of an acrylate group, a methacrylate group, a styrene group, an acryl amide group, a methacryl amide group, a maleate group, a fumarate group, an itaconate group, a vinyl ether group, an allyl ether group, a vinyl ester group, and an allyl ester group;
- n and m independently represent an integer from 1 to 5; and
- A represents an acrylate group and/or a methacrylate group.

4. The polymerizable photoinitiator according to claim 2, wherein A represents an acrylate group.

5. The polymerizable photoinitiator according to claim 1, wherein m represents an integer from 2 to 4.

6. The polymerizable photoinitiator according to claim 5, wherein m represents the integer 2.

7. A polymerizable photoinitiator according to Formula (I):

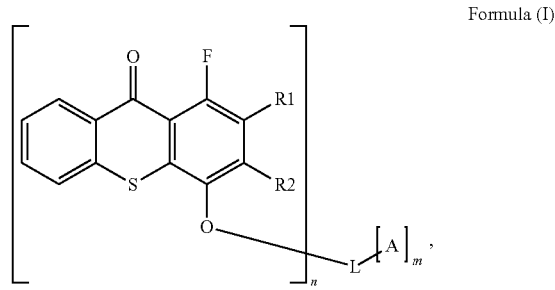

Formula (I)

wherein
- $R^1$ and $R^2$ are independently selected from the group consisting of hydrogen, a substituted or unsubstituted alkyl group, a substituted or unsubstituted alkenyl group, a substituted or unsubstituted alkynyl group, a substituted or unsubstituted aralkyl group, a substituted or unsubstituted alkaryl group, a substituted or unsubstituted aryl or heteroaryl group, a halogen, an ether group, a thioether group, an aldehyde group, a ketone group, an ester group, an amide group, an amine, and a nitro group;
- $R^1$ and $R^2$ may represent the necessary atoms to form a five to eight membered ring;
- L represents an n+m-valent linking group including 1 to 30 carbon atoms;
- A represents a radically polymerizable group selected from the group consisting of an acrylate group, a methacrylate group, a styrene group, an acryl amide group, a methacryl amide group, a maleate group, a fumarate group, an itaconate group, a vinyl ether group, an allyl ether group, a vinyl ester group, and an allyl ester group;
- n and m independently represent an integer from 1 to 5; and the polymerizable photoinitiator is represented by Formula (II):

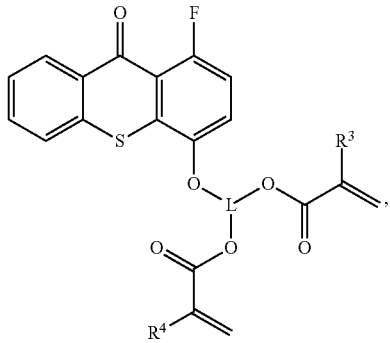

Formula (II)

wherein
L represents a trivalent linking group including 1 to 30 carbon atoms; and
R³ and R⁴ independently represent hydrogen or a methyl group.

8. A polymerizable photoinitiator according to Formula (I):

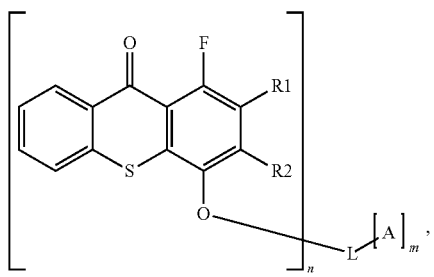

Formula (I)

wherein $R^1$ and $R^2$ are independently selected from the group consisting of hydrogen, a substituted or unsubstituted alkyl group, a substituted or unsubstituted alkenyl group, a substituted or unsubstituted alkynyl group, a substituted or unsubstituted aralkyl group, a substituted or unsubstituted alkaryl group, a substituted or unsubstituted aryl or heteroaryl group, a halogen, an ether group, a thioether group, an aldehyde group, a ketone group, an ester group, an amide group, an amine, and a nitro group;

$R^1$ and $R^2$ may represent the necessary atoms to form a five to eight membered ring;

L represents an n+m-valent linking group including 1 to 30 carbon atoms;

A represents a radically polymerizable group selected from the group consisting of an acrylate group, a methacrylate group, a styrene group, an acryl amide group, a methacryl amide group, a maleate group, a fumarate group, an itaconate group, a vinyl ether group, an allyl ether group, a vinyl ester group, and an allyl ester group;

n and m independently represent an integer from 1 to 5; and
the polymerizable photoinitiator is selected from the group consisting of:

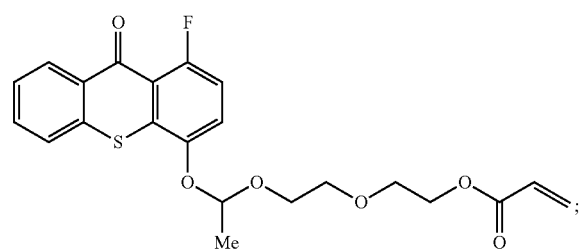

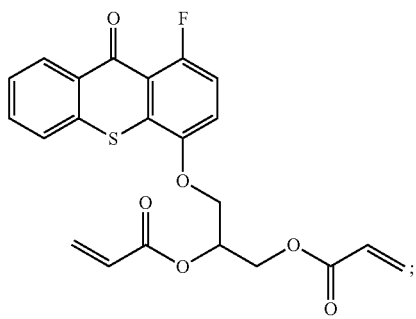

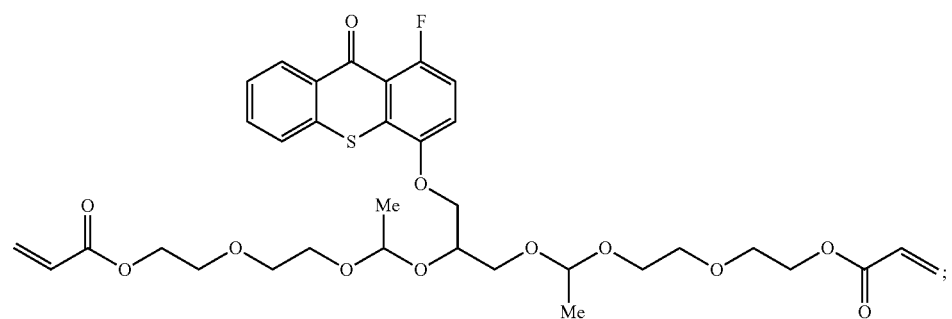

-continued

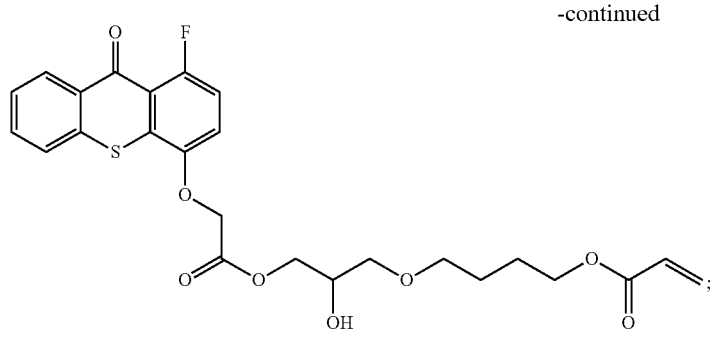
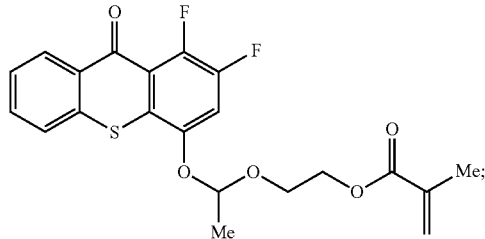
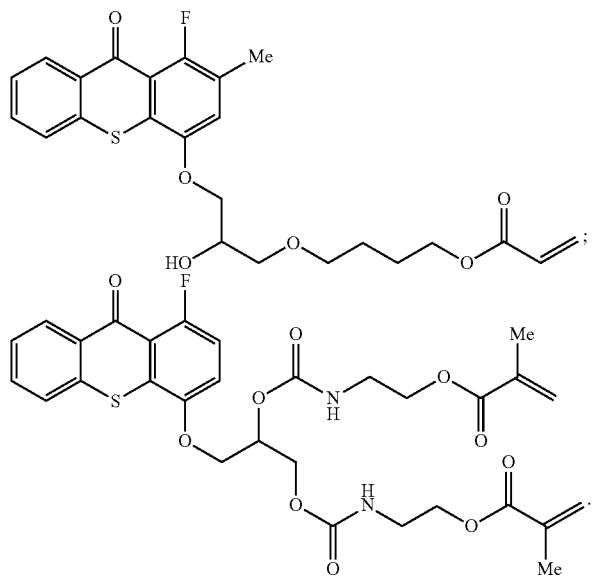
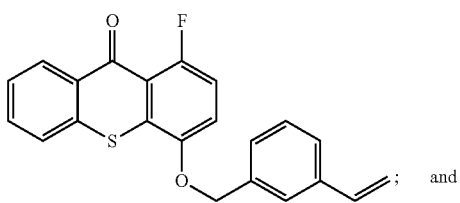

9. A radiation curable composition including:
a polymerizable photoinitiator according to claim 1; and
a monomer according to Formula (III):

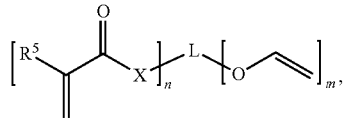

Formula (III)

wherein
m and n independently represent an integer having a value from 1 to 5;
X represents O, S, or $NR^6$;
$R^5$ and $R^6$ independently represent hydrogen or a substituted or unsubstituted alkyl group;
with the proviso that when $X=NR^6$ then L and $R^6$ may together form a ring system; and
L represents a linking group.

10. The radiation curable composition according to claim 9, wherein the radiation curable composition is an inkjet ink having a viscosity of smaller than 10 mPa·s at 45° C. and at a shear rate of 90 $s^{-1}$.

11. A method of preparing a polymerizable photoinitiator including the steps of:

a) providing a monomer according to Formula (III):

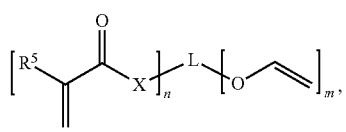

Formula (III)

wherein
m and n independently represent an integer having a value from 1 to 5;
X represents O, S, or $NR^6$;
$R^5$ and $R^6$ independently represent hydrogen or a substituted or unsubstituted alkyl group;
with the proviso that when $X=NR^6$ then L and $R^6$ may together form a ring system; and
L represents a linking group;

b) providing a photoinitiator according to Formula (Ia):

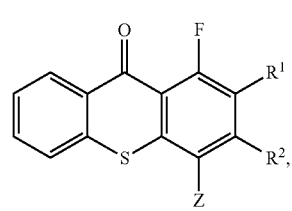

Formula (Ia)

wherein
- R¹ and R² are independently selected from the group consisting of hydrogen, a substituted or unsubstituted alkyl group, a substituted or unsubstituted alkenyl group, a substituted or unsubstituted alkynyl group, a substituted or unsubstituted aralkyl group, a substituted or unsubstituted alkaryl group, a substituted or unsubstituted aryl or heteroaryl group, a halogen, an ether group, a thioether group, an aldehyde group, a ketone group, an ester group, an amide group, an amine, and a nitro group;
- R¹ and R² may represent the necessary atoms to form a five to eight membered ring; and
- Z represents a hydroxyl group or an alkoxy group including at least one hydroxyl group; and
- c) catalyzing a reaction between the monomer and the photoinitiator with a catalyst to form a polymerizable photoinitiator as defined by claim 1.

12. The method according to claim 11, wherein the catalyst is selected from the group consisting of trifluoroacetic acid, trichloroacetic acid, pyridinium tosylate, crosslinked poly(vinylpyridine) hydrochloride, poly(vinylpyridinium) tosylate, and sulfonic acid substituted ion exchangers.

13. The method according to claim 11, wherein the polymerizable photoinitiator is not isolated after its synthesis.

\* \* \* \* \*